(12) United States Patent
Turner et al.

(10) Patent No.: US 12,233,170 B2
(45) Date of Patent: *Feb. 25, 2025

(54) ABSORBENT ARTICLE COMPRISING A LOTION RESISTANT POLYMERIC FILLER COMPOSITION

(71) Applicant: The Procter & Gamble Company, Cincinnati, OH (US)

(72) Inventors: Robert Haines Turner, Cincinnati, OH (US); John Andrew Strasemeier, Aurora, IN (US)

(73) Assignee: The Procter & Gamble Company, Cincinnati, OH (US)

( * ) Notice: Subject to any disclaimer, the term of this patent is extended or adjusted under 35 U.S.C. 154(b) by 57 days.

This patent is subject to a terminal disclaimer.

(21) Appl. No.: 18/327,099

(22) Filed: Jun. 1, 2023

(65) Prior Publication Data

US 2023/0338606 A1 Oct. 26, 2023

Related U.S. Application Data

(63) Continuation of application No. 16/590,420, filed on Oct. 2, 2019, now Pat. No. 11,707,548.

(Continued)

(51) Int. Cl.
*A61F 13/15* (2006.01)
*A61L 15/22* (2006.01)
(Continued)

(52) U.S. Cl.
CPC ............ *A61L 15/225* (2013.01); *A61F 13/15* (2013.01); *A61L 15/42* (2013.01); *A61L 15/58* (2013.01);
(Continued)

(58) Field of Classification Search
CPC .... A61F 13/15; A61F 13/15203; A61F 13/53; A61F 2013/15292; A61F 2013/15357;
(Continued)

(56) References Cited

U.S. PATENT DOCUMENTS 2,531,036 A 11/1950 Goettsch
3,445,915 A 5/1969 Cuckson et al.
(Continued)

FOREIGN PATENT DOCUMENTS

CN 201088947 Y 7/2008
DE 8802807 U1 6/1988
(Continued)

OTHER PUBLICATIONS

PCT Search Report and Written Opinion for PCT/US2019/055332 dated Jan. 15, 2020; 15 pages.
(Continued)

*Primary Examiner* — Catharine L Anderson
(74) *Attorney, Agent, or Firm* — Anna E. Haller; Amanda Marie Herman Berghauer

(57) ABSTRACT

Described herein is an absorbent article including (a) an absorbent core, a first nonwoven material, a second nonwoven material, and a bond area; and (b) a polymeric filler composition disposed within the bond area. The polymeric filler composition has less than 5% of a tackifier. The polymeric filler composition is chosen from a propylene butene copolymer, a polypropylene homopolymer, a propylene ethylene copolymer, and mixtures thereof. The polymeric filler composition has a Tensile Strength at Yield of from about 0.5 MPa to about 10 MPa.

12 Claims, 14 Drawing Sheets

Related U.S. Application Data

(60) Provisional application No. 62/743,266, filed on Oct. 9, 2018.

(51) Int. Cl.
   *A61L 15/42* (2006.01)
   *A61L 15/58* (2006.01)

(52) U.S. Cl.
   CPC ............. *A61F 2013/15292* (2013.01); *A61F 2013/15569* (2013.01)

(58) Field of Classification Search
   CPC .......... A61F 2013/15569; A61F 2013/530182; A61F 2013/530189; A61F 2013/530218; A61L 15/225; A61L 15/42; A61L 15/58
   See application file for complete search history.

(56) References Cited

U.S. PATENT DOCUMENTS

| | | |
|---|---|---|
| 3,860,003 A | 1/1975 | Buell |
| 4,022,211 A | 5/1977 | Timmons |
| 4,082,059 A | 4/1978 | Mcintyre et al. |
| 4,133,774 A | 1/1979 | Brynko |
| 4,135,024 A | 1/1979 | Callahan et al. |
| 4,167,914 A | 9/1979 | Mladota |
| 4,277,301 A | 7/1981 | Mcintyre et al. |
| 4,357,370 A | 11/1982 | Alheid |
| 4,481,068 A | 11/1984 | Richey |
| 4,610,678 A | 9/1986 | Weisman et al. |
| 4,673,402 A | 6/1987 | Weisman et al. |
| 4,695,278 A | 9/1987 | Lawson |
| 4,704,115 A | 11/1987 | Buell |
| 4,748,044 A | 5/1988 | Fottinger et al. |
| 4,795,454 A | 1/1989 | Dragoo |
| 4,834,735 A | 5/1989 | Alemany et al. |
| 4,876,982 A | 10/1989 | Claassen |
| 4,888,231 A | 12/1989 | Angstadt |
| 4,909,803 A | 3/1990 | Aziz |
| 4,917,696 A | 4/1990 | De |
| 4,943,451 A | 7/1990 | Zimmer |
| 5,168,806 A | 12/1992 | Reder et al. |
| 5,286,543 A | 2/1994 | Ungpiyakul |
| 5,302,675 A | 4/1994 | Sustic |
| 5,359,525 A | 10/1994 | Weyenberg |
| 5,500,075 A | 3/1996 | Herrmann |
| 5,525,175 A | 6/1996 | Blenke et al. |
| 5,538,754 A | 7/1996 | Sandock |
| 5,562,646 A | 10/1996 | Goldman |
| 5,599,335 A | 2/1997 | Goldman |
| 5,624,775 A | 4/1997 | Carre et al. |
| 5,628,097 A | 5/1997 | Benson |
| 5,654,040 A | 8/1997 | Matsunaga |
| 5,669,894 A | 9/1997 | Goldman |
| 5,723,546 A | 3/1998 | Sustic |
| 5,759,274 A | 6/1998 | Maier et al. |
| 5,792,262 A | 8/1998 | Bohn et al. |
| 5,827,609 A | 10/1998 | Ercillo et al. |
| 5,916,661 A | 6/1999 | Benson |
| 6,003,513 A | 12/1999 | Readey et al. |
| 6,033,513 A | 3/2000 | Nakamura |
| 6,074,480 A | 6/2000 | Kakuta |
| 6,107,539 A | 8/2000 | Palumbo |
| 6,193,918 B1 | 2/2001 | Mcguire et al. |
| 6,217,690 B1 | 4/2001 | Rajala et al. |
| 6,284,081 B1 | 9/2001 | Vogt et al. |
| 6,287,409 B1 | 9/2001 | Stephany |
| 6,297,424 B1 | 10/2001 | Olson |
| 6,426,119 B1 | 7/2002 | Yapel et al. |
| 6,432,242 B1 | 8/2002 | Nielsen et al. |
| 6,524,660 B2 | 2/2003 | Quiel et al. |
| 6,531,027 B1 | 3/2003 | Lender et al. |
| 6,545,197 B1 | 4/2003 | Muller |
| 6,569,275 B1 | 5/2003 | Coenen et al. |
| 6,582,543 B1 | 6/2003 | Nilsson et al. |
| 6,582,829 B1 | 6/2003 | Quinn |
| 6,585,841 B1 | 7/2003 | Coenen et al. |
| 6,589,149 B1 | 7/2003 | Vaneperen et al. |
| 6,602,454 B2 | 8/2003 | Mcguire et al. |
| 6,645,190 B1 | 11/2003 | Olson et al. |
| 6,699,347 B2 | 3/2004 | Lehrter et al. |
| 6,761,711 B1 | 7/2004 | Fletcher et al. |
| 6,790,798 B1 | 9/2004 | Suzuki |
| 6,801,828 B2 | 10/2004 | Popp |
| 6,808,582 B2 | 10/2004 | Coenen et al. |
| 6,817,994 B2 | 11/2004 | Popp et al. |
| 6,820,022 B2 | 11/2004 | Coenen |
| 6,840,928 B2 | 1/2005 | Datta et al. |
| 6,849,067 B2 | 2/2005 | Fletcher et al. |
| 6,881,471 B2 | 4/2005 | Toussant et al. |
| 6,893,426 B1 | 5/2005 | Popp et al. |
| 6,942,894 B2 | 9/2005 | Alberg |
| 6,953,452 B2 | 10/2005 | Popp et al. |
| 6,969,377 B2 | 11/2005 | Koele et al. |
| 7,045,031 B2 | 5/2006 | Coenen et al. |
| 7,056,386 B2 | 6/2006 | Pahl |
| 7,097,725 B2 | 8/2006 | Yoneoka et al. |
| 7,123,981 B2 | 10/2006 | Dollevoet |
| 7,156,833 B2 | 1/2007 | Couture-Dorschner et al. |
| 7,163,740 B2 | 1/2007 | Rosati et al. |
| 7,201,744 B2 | 4/2007 | Van Gompel et al. |
| 7,252,855 B2 | 8/2007 | Haskett et al. |
| 7,432,413 B2 | 10/2008 | Roe |
| 7,444,932 B2 | 11/2008 | Strand et al. |
| 7,460,250 B2 | 12/2008 | Keightley et al. |
| 7,489,410 B2 | 2/2009 | Nishio |
| 7,497,851 B2 | 3/2009 | Koele et al. |
| 7,569,039 B2 | 8/2009 | Matsuda |
| 7,611,582 B2 | 11/2009 | Mcneil et al. |
| 7,625,605 B2 | 12/2009 | Cooprider et al. |
| 7,667,857 B2 | 2/2010 | Nishio |
| 7,682,349 B2 | 3/2010 | Popp et al. |
| 7,736,456 B2 | 6/2010 | Branca et al. |
| 7,752,995 B2 | 7/2010 | Tremblay et al. |
| 7,766,887 B2 | 8/2010 | Burns, Jr. et al. |
| 7,862,550 B2 | 1/2011 | Koele et al. |
| 7,901,393 B2 | 3/2011 | Matsuda et al. |
| 8,007,485 B2 | 8/2011 | Popp et al. |
| 8,145,343 B2 | 3/2012 | Debruler |
| 8,145,344 B2 | 3/2012 | Debruler |
| 8,163,332 B2 | 4/2012 | Emoto et al. |
| 8,186,296 B2 | 5/2012 | Brown |
| 8,244,393 B2 | 8/2012 | McLaughlin |
| 8,361,048 B2 | 1/2013 | Kuen et al. |
| 8,372,052 B2 | 2/2013 | Popp et al. |
| 8,445,067 B2 | 5/2013 | Suzuki et al. |
| 8,574,668 B2 | 11/2013 | Brown et al. |
| 8,579,876 B2 | 11/2013 | Popp et al. |
| 8,703,450 B2 | 4/2014 | Bub et al. |
| 8,747,379 B2 | 6/2014 | Fletcher et al. |
| 8,771,449 B2 | 7/2014 | Takino et al. |
| 9,169,366 B2 | 10/2015 | Weisman et al. |
| 9,265,672 B2 | 2/2016 | Brown |
| 9,295,590 B2 | 3/2016 | Brown |
| 9,421,137 B2 | 8/2016 | Lavon |
| 9,498,389 B2 | 11/2016 | Trennepohl |
| 9,630,901 B2 | 4/2017 | Godlewski et al. |
| 9,808,827 B2 | 11/2017 | Brown et al. |
| 9,822,197 B2 | 11/2017 | Hörner et al. |
| 9,872,801 B2 | 1/2018 | Hammons |
| 11,707,548 B2 * | 7/2023 | Turner .................. A61L 15/225 604/372 |
| 2001/0053898 A1 | 12/2001 | Olson et al. |
| 2002/0007162 A1 | 1/2002 | Cammarota et al. |
| 2003/0138570 A1 | 7/2003 | Kaylor et al. |
| 2004/0091701 A1 | 5/2004 | Toussant et al. |
| 2004/0097895 A1 | 5/2004 | Busam |
| 2004/0102125 A1 | 5/2004 | Morman et al. |
| 2004/0158212 A1 | 8/2004 | Ponomarenko |
| 2005/0087292 A1 | 4/2005 | Mcfall et al. |
| 2005/0107764 A1 | 5/2005 | Matsuda |
| 2005/0233072 A1 | 10/2005 | Stephan et al. |
| 2006/0021695 A1 | 2/2006 | Blessing |
| 2006/0048880 A1 | 3/2006 | Blessing |

(56) References Cited

U.S. PATENT DOCUMENTS

| | | |
|---|---|---|
| 2006/0073320 A1 | 4/2006 | Pervan |
| 2006/0153984 A1 | 7/2006 | Suzuki |
| 2007/0003736 A1 | 1/2007 | Saarvali et al. |
| 2007/0065574 A1 | 3/2007 | Rosati et al. |
| 2007/0142798 A1 | 6/2007 | Goodlander |
| 2007/0219521 A1 | 9/2007 | Hird |
| 2007/0287983 A1 | 12/2007 | Lodge |
| 2008/0081868 A1 | 4/2008 | Jiang |
| 2008/0114319 A1 | 5/2008 | Burns et al. |
| 2008/0132865 A1 | 6/2008 | Li et al. |
| 2008/0215166 A1 | 9/2008 | Blessing |
| 2008/0221543 A1 | 9/2008 | Wilkes et al. |
| 2008/0245298 A1 | 10/2008 | Ayers |
| 2009/0312730 A1 | 12/2009 | Lavon |
| 2010/0051166 A1 | 3/2010 | Hundorf |
| 2010/0059178 A1 | 3/2010 | Jiang |
| 2010/0078127 A1 | 4/2010 | Yamamoto et al. |
| 2010/0193138 A1 | 8/2010 | Eckstein et al. |
| 2010/0224318 A1 | 9/2010 | Morita |
| 2010/0230056 A1 | 9/2010 | Aono |
| 2010/0252178 A1 | 10/2010 | Takino et al. |
| 2010/0264369 A1 | 10/2010 | Zhang |
| 2010/0286644 A1 | 11/2010 | Li |
| 2011/0036487 A1 | 2/2011 | Rajala et al. |
| 2011/0137274 A1 | 6/2011 | Klofta |
| 2011/0139657 A1 | 6/2011 | Hird |
| 2011/0139658 A1 | 6/2011 | Hird |
| 2011/0139659 A1 | 6/2011 | Hird |
| 2011/0139662 A1 | 6/2011 | Hird |
| 2011/0152812 A1 | 6/2011 | Hird |
| 2011/0172629 A1 | 7/2011 | Roe et al. |
| 2011/0274834 A1 | 11/2011 | Brown et al. |
| 2012/0061015 A1 | 3/2012 | Lavon |
| 2012/0061016 A1 | 3/2012 | Lavon |
| 2012/0111975 A1 | 5/2012 | Ogasawara |
| 2012/0116341 A1 | 5/2012 | Corzani et al. |
| 2012/0152441 A1 | 6/2012 | Rajala |
| 2012/0273129 A1 | 11/2012 | Handziak |
| 2012/0316046 A1 | 12/2012 | Jackels et al. |
| 2013/0129925 A1 | 5/2013 | Hanai et al. |
| 2013/0202787 A1 | 8/2013 | Hu |
| 2013/0211363 A1 | 8/2013 | LaVon et al. |
| 2013/0255861 A1 | 10/2013 | Schneider |
| 2013/0255862 A1 | 10/2013 | Schneider |
| 2013/0255863 A1 | 10/2013 | Lavon |
| 2013/0255864 A1 | 10/2013 | Schneider |
| 2013/0255865 A1 | 10/2013 | Brown |
| 2013/0287953 A1 | 10/2013 | Mcguire et al. |
| 2014/0005020 A1 | 1/2014 | Lavon et al. |
| 2014/0057058 A1 | 2/2014 | Yapel et al. |
| 2014/0144579 A1 | 5/2014 | Brown et al. |
| 2014/0148323 A1 | 5/2014 | Brown et al. |
| 2014/0148773 A1 | 5/2014 | Brown |
| 2014/0296811 A1 | 10/2014 | Bunnelle |
| 2014/0330238 A1 | 11/2014 | Schönbeck |
| 2015/0342797 A1 | 12/2015 | Jackels |
| 2015/0352589 A1 | 12/2015 | Brown |
| 2016/0053149 A1 | 2/2016 | Herrlich |
| 2016/0136014 A1 | 5/2016 | Arora |
| 2016/0206774 A1 | 7/2016 | Hird |
| 2016/0270986 A1 | 9/2016 | Stiehl et al. |
| 2016/0270987 A1 | 9/2016 | Stiehl et al. |
| 2017/0165130 A1 | 6/2017 | Turner |
| 2017/0165133 A1 | 6/2017 | Turner |
| 2018/0221911 A1 | 8/2018 | Jackels |
| 2018/0333514 A1 | 11/2018 | Misra |
| 2019/0002737 A1 | 1/2019 | Runge |
| 2020/0108167 A1 | 4/2020 | Turner et al. |
| 2020/0108168 A1 | 4/2020 | Turner et al. |
| 2020/0222579 A1 | 7/2020 | Turner |
| 2020/0330287 A1 | 10/2020 | Brown et al. |
| 2020/0330291 A1 | 10/2020 | Lindner et al. |
| 2021/0316036 A1 | 10/2021 | Strasemeier et al. |
| 2023/0338606 A1 | 10/2023 | Turner |

FOREIGN PATENT DOCUMENTS

| | | |
|---|---|---|
| DE | 102006040702 A1 | 3/2008 |
| DE | 102011076748 A1 | 12/2011 |
| EP | 0372120 A2 | 6/1990 |
| EP | 0380781 A2 | 8/1990 |
| EP | 0221932 B1 | 10/1990 |
| EP | 0535579 A1 | 4/1993 |
| EP | 0730914 A2 | 9/1996 |
| EP | 0745368 A1 | 12/1996 |
| EP | 0788408 B1 | 11/2001 |
| EP | 0923616 B1 | 9/2003 |
| EP | 1621166 A1 | 2/2006 |
| EP | 1855883 B1 | 12/2008 |
| EP | 2191959 A1 | 6/2010 |
| EP | 1863594 B1 | 1/2011 |
| EP | 2420325 A2 | 2/2012 |
| EP | 2520426 A1 | 11/2012 |
| FR | 2873382 A1 | 1/2006 |
| JP | S62149367 A | 7/1987 |
| JP | 2005046805 A | 2/2005 |
| JP | 2007143676 A | 6/2007 |
| JP | 2009233506 A | 10/2009 |
| KR | 20090101705 A | 9/2009 |
| WO | 9604874 A1 | 2/1996 |
| WO | 0076438 A2 | 12/2000 |
| WO | 0076443 A1 | 12/2000 |
| WO | 2005014263 A1 | 2/2005 |
| WO | 2006098934 A1 | 9/2006 |
| WO | 2008038563 A1 | 4/2008 |
| WO | 2012026330 A1 | 3/2012 |
| WO | 2014085063 A1 | 6/2014 |
| WO | 2015094960 A1 | 6/2015 |
| WO | 2015191802 A1 | 12/2015 |
| WO | 2018098431 A1 | 5/2018 |
| WO | 2020076906 A1 | 4/2020 |

OTHER PUBLICATIONS

All Office Actions; U.S. Appl. No. 16/590,420, filed Oct. 2, 2019.
All Office Actions; U.S. Appl. No. 13/685,817, filed Nov. 27, 2012.
All Office Actions; U.S. Appl. No. 14/993,154, filed Jan. 12, 2016.
All Office Actions; U.S. Appl. No. 16/597,146, filed Oct. 9, 2019.
All Office Actions; U.S. Appl. No. 17/225,168, filed Apr. 8, 2021.
Ioannis M. Kalogeras, "Glass-Transition Phenomena in Polymer Blends", Encyclopedia of Polymer Blends, vol. 3, Chapter 1, 2016, pp. 1-134.
Unpublished U.S. Appl. No. 18/587,033, filed Feb. 26, 2024, Lindner Torsten et al.

* cited by examiner

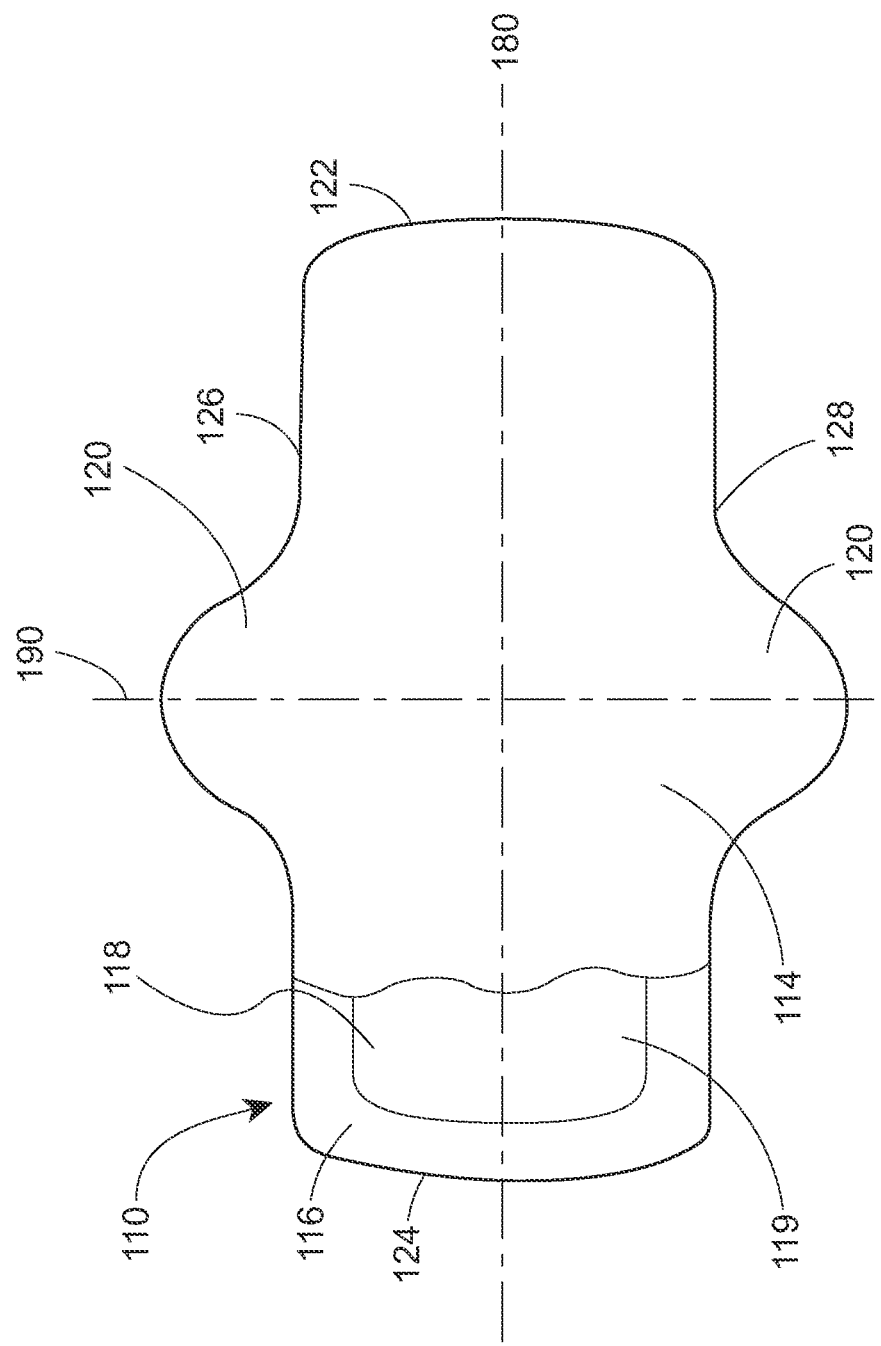

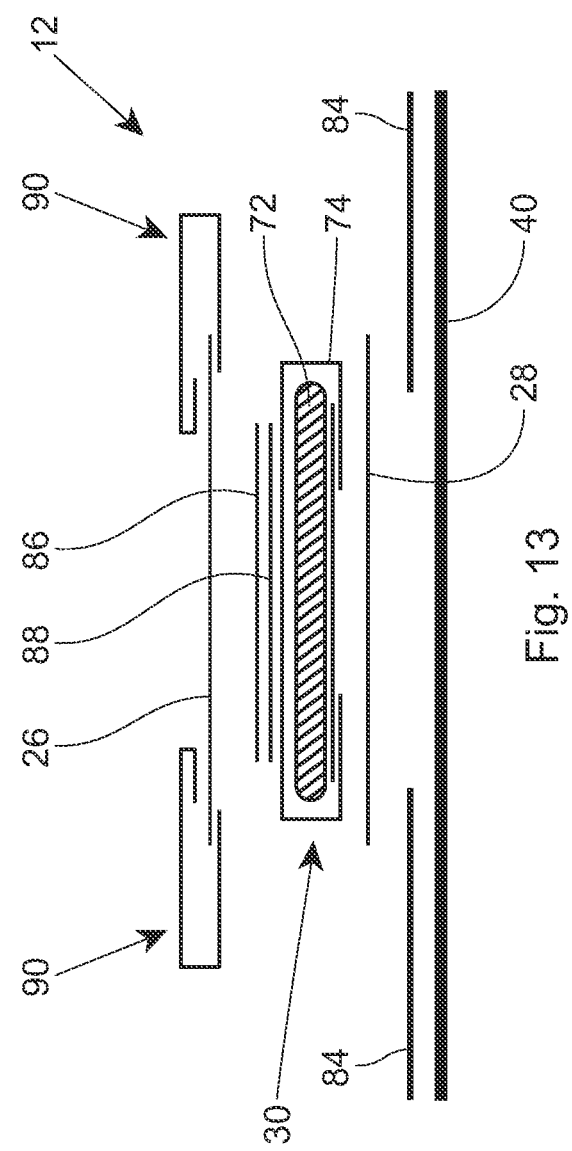

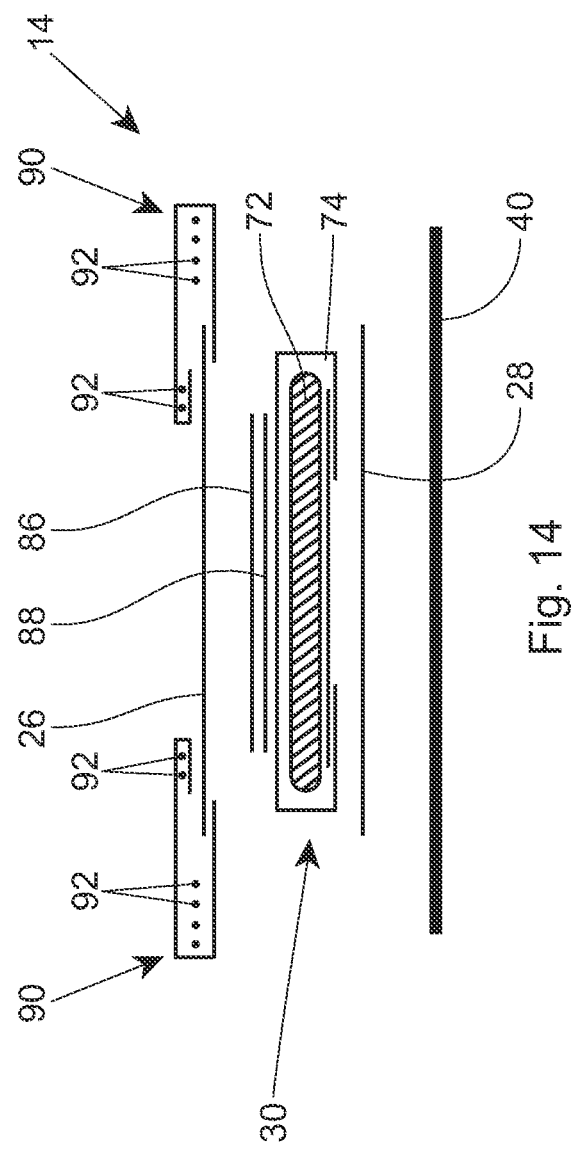

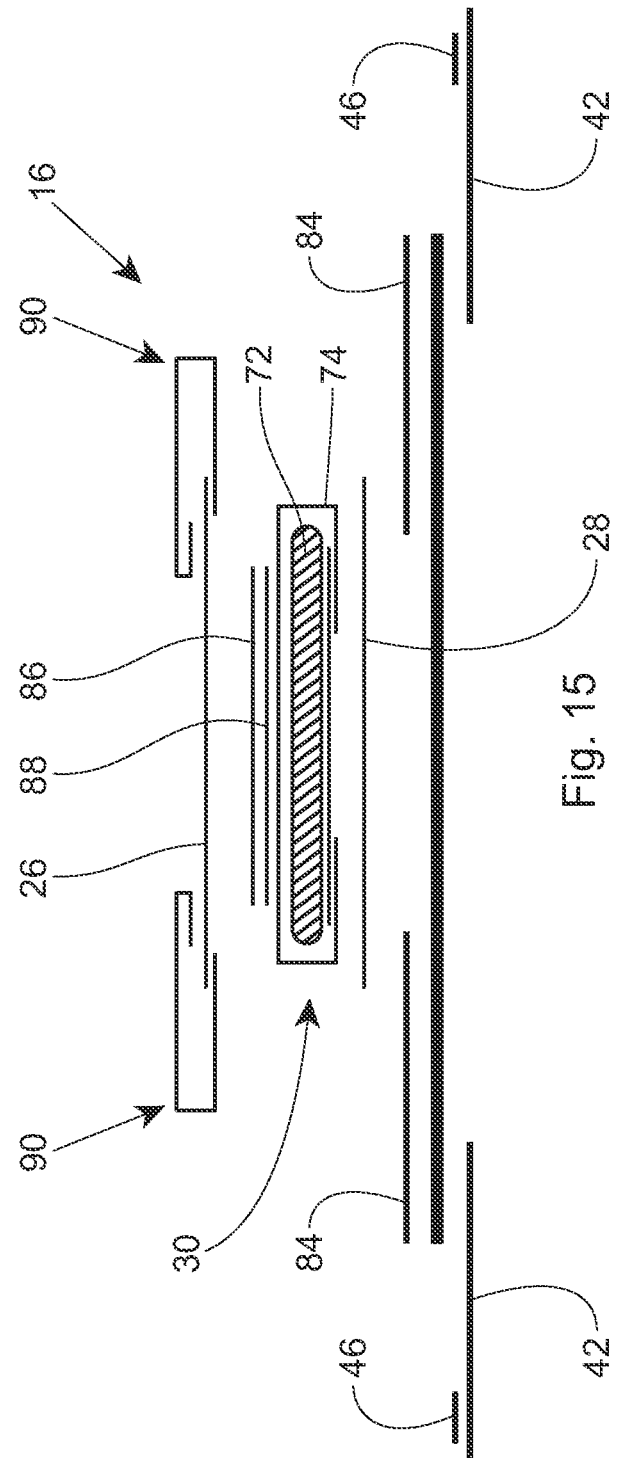

ABSORBENT ARTICLE COMPRISING A LOTION RESISTANT POLYMERIC FILLER COMPOSITION

CROSS REFERENCE TO RELATED APPLICATIONS

This application is a continuation of, and claims priority under 35 U.S.C. § 120 to U.S. patent application Ser. No. 16/590,420, filed on Oct. 2, 2019, which claims the benefit, under 35 USC § 119(e), of U.S. Provisional Patent Application Ser. No. 62/743,266, filed on Oct. 9, 2018, the entire disclosures of which are fully incorporated by reference herein.

FIELD

Described herein in is an absorbent article comprising an absorbent core, a first nonwoven material, a second nonwoven material, a bond area, and a lotion resistant, substantially tackifier-free polymeric filler composition disposed within the bond area. The polymeric filler composition may be selected from the group consisting of a propylene butene copolymer, a polypropylene homopolymer, a propylene ethylene copolymer, and mixtures thereof.

BACKGROUND

Users, for example caregivers, rely on disposable absorbent articles to make their lives easier. Disposable absorbent articles, such as adult incontinence articles, diapers, and training pants are generally manufactured by combining several components. These components typically include a chassis comprising a liquid-permeable topsheet, a liquid-impermeable backsheet attached to the topsheet, an absorbent core located between the topsheet and the backsheet, and a plurality of bond areas holding the chassis together. When the disposable article is worn, the liquid-permeable topsheet is positioned next to the body of the wearer. The topsheet allows passage of bodily fluids into the absorbent core. The liquid-impermeable backsheet helps prevent leakage of fluids held in the absorbent core. The absorbent core generally is designed to have desirable physical properties, e.g. a high absorbent capacity and high absorption rate, so that bodily fluids can be transported from the skin of the wearer into the disposable absorbent article.

Frequently one or more components of a disposable absorbent article are bonded together. For example, hot melt adhesives have been used to bond individual layers of the chassis of the absorbent article, such as the topsheet and backsheet together. Hot melt adhesives have also been used to bond discrete components, such as fasteners and leg elastics or cuffs, to the article. The hot melt adhesive is often called a construction adhesive because it is used to help construct the absorbent article from individual components.

Common hot melt adhesives are made by combining polymer and additive components in a substantially uniform thermoplastic blend. Typical additives include tackifiers, plasticizers, and/or waxes, for example. While such formulations generally work, they can be costly and their performance properties can be improved. For example, tackifiers, which can comprise up to 65% of an adhesive formula, can be expensive and difficult to source. Therefore, there is a need for improved hot melt adhesives, such as substantially tackifier-free polymeric filler compositions, that offer (1) superior performance compared to tackifier-based hot melt adhesives (2) at a lower cost.

In addition, common hot melt adhesives holding a bond area together often perform poorly when exposed to various skin-protective materials. Therefore, there is a need for improved hot melt adhesives, such as substantially tackifier-free polymeric filler compositions, that offer (1) superior lotion resistance after exposure to various skin-protective materials (2) at a lower cost.

SUMMARY

Described herein is an absorbent article comprising: (a) an absorbent core, a first nonwoven material, a second nonwoven material, and a bond area; and (b) a polymeric filler composition disposed within the bond area; wherein the polymeric filler composition comprises less than 1% of a tackifier by weight of the polymeric filler composition; wherein the polymeric filler composition is selected from the group consisting of a propylene butene copolymer, a polypropylene homopolymer, a propylene ethylene copolymer, and mixtures thereof; wherein the polymeric filler composition has a Tensile Strength at Yield of from about 0.5 MPa to about 10 MPa according to the Tensile Strength Test Method described herein; and wherein the bond area has a Peak Peel Strength of from about 0.1 N/cm to about 9 N/cm after exposure to a skin-protecting material for 24 hours according to the Laminate Peel Test Method described herein.

Also described herein is a method comprising: (a) providing an absorbent article comprising an absorbent core, a first nonwoven material, a second nonwoven material, and a bond area; wherein the bond area comprises a portion of the first nonwoven material, a portion of the second nonwoven material, and a polymeric filler composition; wherein the polymeric filler composition is disposed within the bond area; wherein the polymeric filler composition comprises less than 1% of a tackifier by weight of the polymeric filler composition; wherein the polymeric filler composition is selected from the group consisting of a propylene butene copolymer, a polypropylene homopolymer, a propylene ethylene copolymer, and mixtures thereof; and wherein the polymeric filler composition has a Tensile Strength at Yield of from about 0.5 MPa to about 10 MPa according to the Tensile Strength Test Method described herein; (b) bringing the bond area in contact with a skin-protecting material; wherein the bond area has a Peak Peel Strength of from about 0.1 N/cm to about 9 N/cm after exposure to the skin-protecting material for 24 hours according to the Laminate Peel Test Method described herein.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein:

FIG. 12 is a plan view of an example absorbent article of the present disclosure that is a sanitary napkin;

FIG. 13 is an example cross-sectional view taken within a front waist region of an absorbent article;

FIG. 14 is an example cross-sectional view taken within a crotch region of an absorbent article; and FIG. 15 is an example cross-sectional view taken within a back waist region of an absorbent article.

DETAILED DESCRIPTION

Various non-limiting forms of the present disclosure will now be described to provide an overall understanding of the principles of the structure, function, manufacture, and use of the absorbent article comprising a lotion resistant polymeric filler composition described herein. One or more examples of these non-limiting forms are illustrated in the accompanying drawings. Those of ordinary skill in the art will understand that the absorbent article comprising a lotion resistant polymeric filler composition described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

General Description of Absorbent Article

Figure 1:
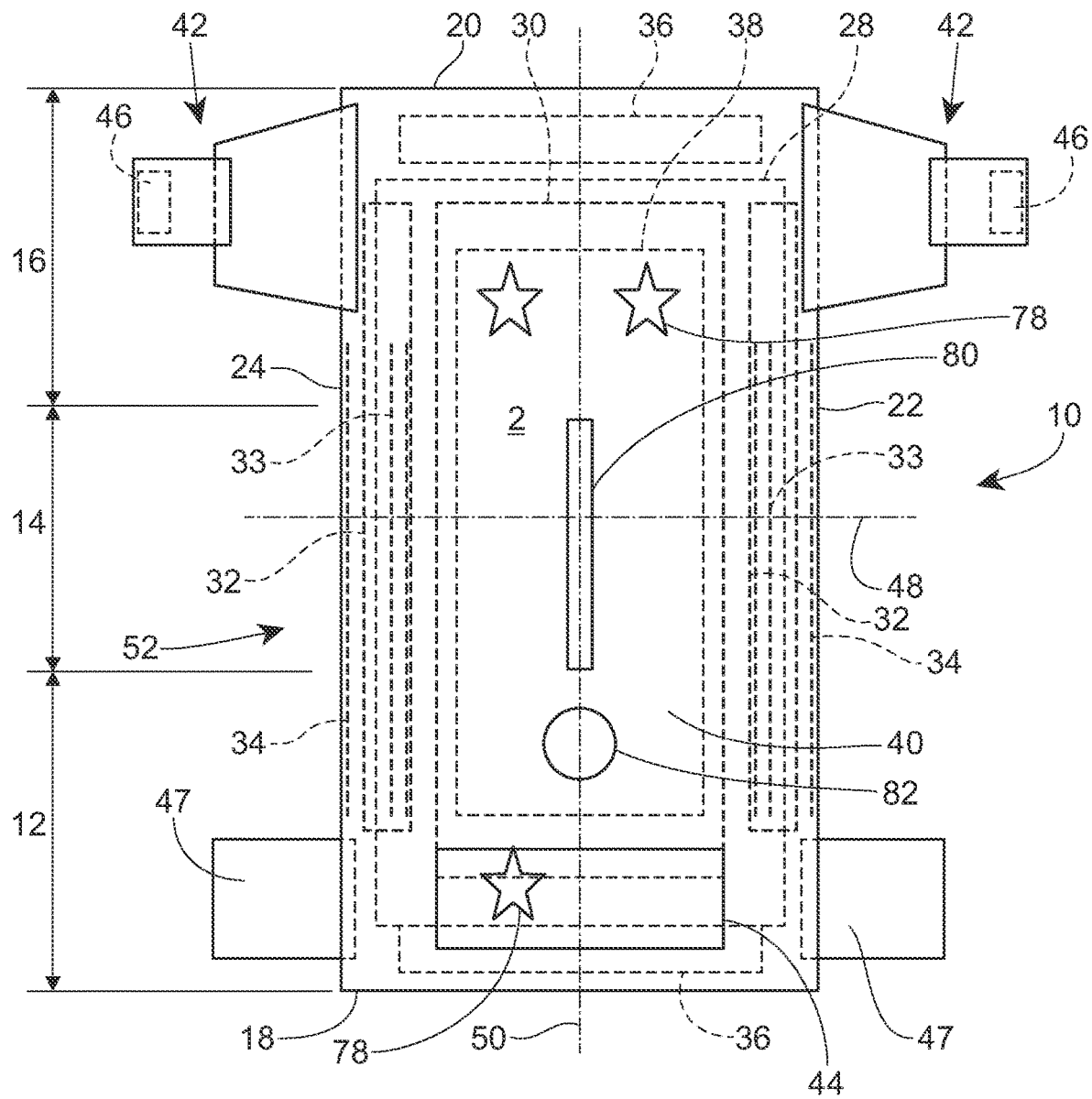
FIG. 1 is a plan view of an example absorbent article in the form of a taped diaper, garment-facing surface facing the viewer, in a flat laid-out state.
Figure 2:
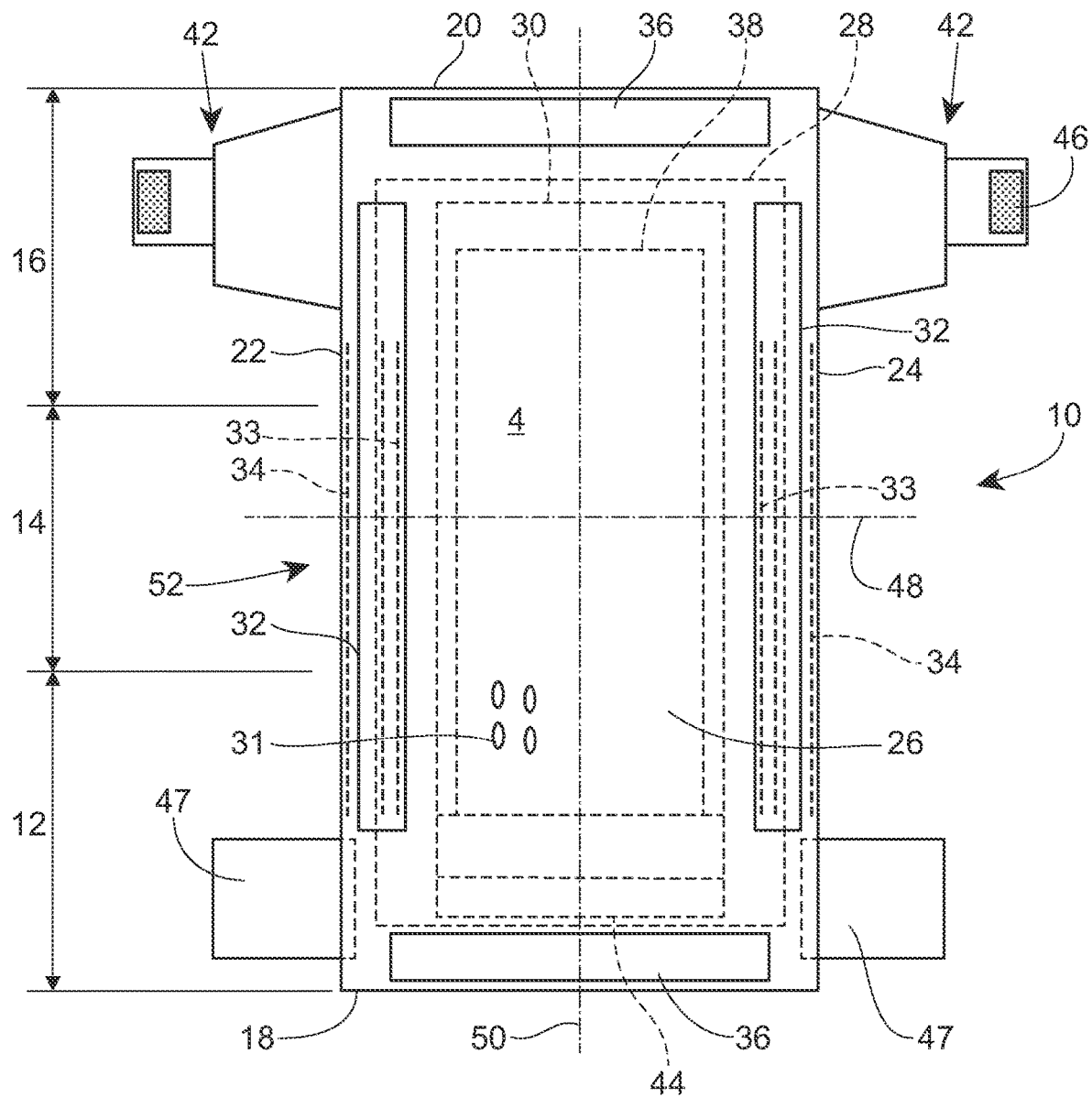
FIG. 2 is a plan view of the example absorbent article of FIG. 1, wearer-facing surface facing the viewer, in a flat laid-out state.
Figure 3:
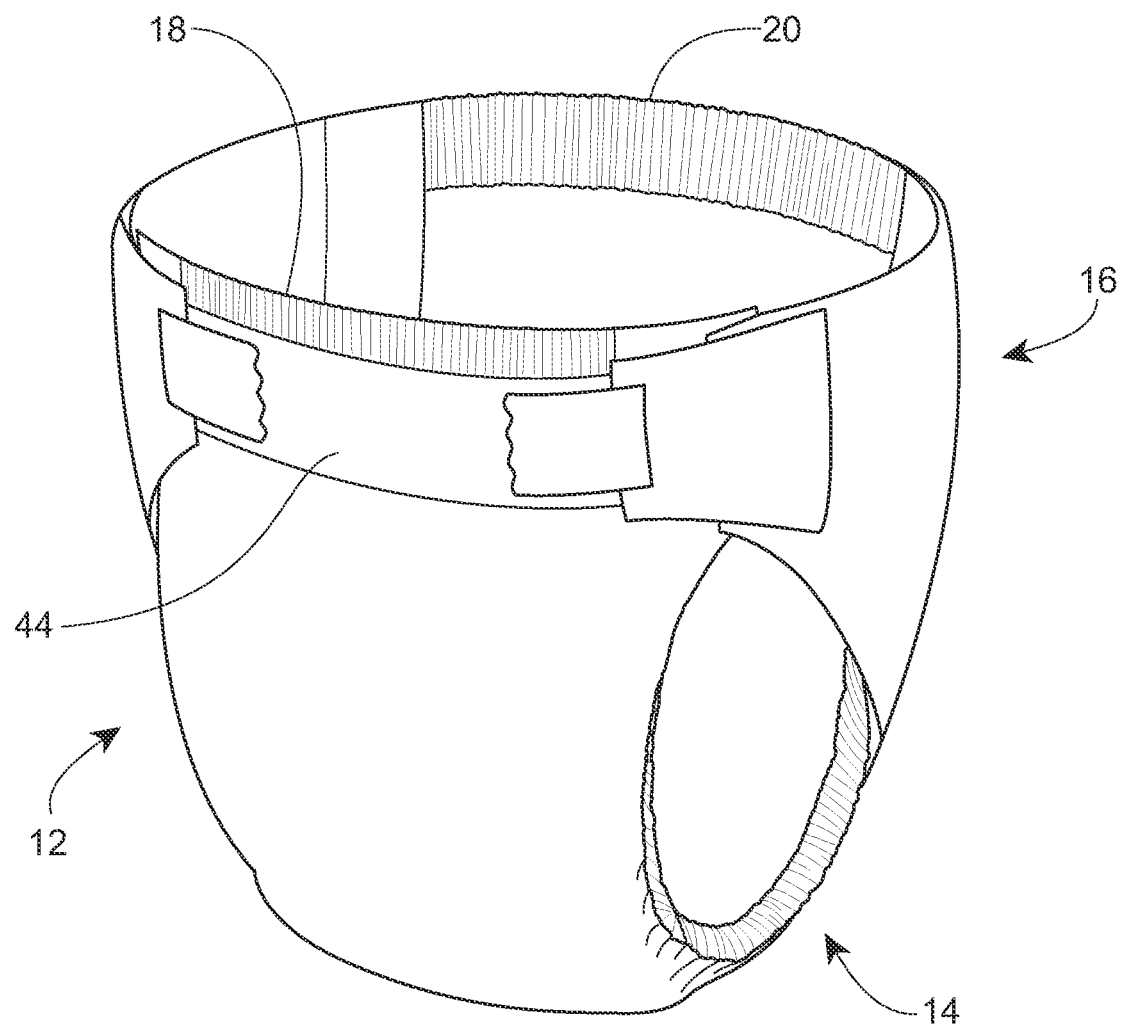
FIG. 3 is a front perspective view of the absorbent article of FIGS. 1 and 2 in a fastened position.

An example absorbent article 10 according to the present disclosure, shown in the form of a taped diaper, is represented in FIGS. 1-3. FIG. 1 is a plan view of the example absorbent article 10, garment-facing surface 2 facing the viewer in a flat, laid-out state (i.e., no elastic contraction). FIG. 2 is a plan view of the example absorbent article 10 of FIG. 1, wearer-facing surface 4 facing the viewer in a flat, laid-out state. FIG. 3 is a front perspective view of the absorbent article 10 of FIGS. 1 and 2 in a fastened configuration. The absorbent article 10 of FIGS. 1-3 is shown for illustration purposes only as the present disclosure may be used for making a wide variety of diapers, including adult incontinence products, pants, or other absorbent articles, such as sanitary napkins and absorbent pads, for example.

The absorbent article 10 may comprise a front waist region 12, a crotch region 14, and a back waist region 16. The crotch region 14 may extend intermediate the front waist region 12 and the back waist region 16. The front wait region 12, the crotch region 14, and the back waist region 16 may each be ⅓ of the length of the absorbent article 10. The absorbent article 10 may comprise a front end edge 18, a back end edge 20 opposite to the front end edge 18, and longitudinally extending, transversely opposed side edges 22 and 24 defined by the chassis 52.

The absorbent article 10 may comprise a liquid permeable topsheet 26, a liquid impermeable backsheet 28, and an absorbent core 30 positioned at least partially intermediate the topsheet 26 and the backsheet 28. The absorbent article 10 may also comprise one or more pairs of barrier leg cuffs 32 with or without elastics 33, one or more pairs of leg elastics 34, one or more elastic waistbands 36, and/or one or more acquisition materials 38. The acquisition material or materials 38 may be positioned intermediate the topsheet 26 and the absorbent core 30. An outer cover material 40, such as a nonwoven material, may cover a garment-facing side of the backsheet 28. The absorbent article 10 may comprise back ears 42 in the back waist region 16. The back ears 42 may comprise fasteners 46 and may extend from the back waist region 16 of the absorbent article 10 and attach (using the fasteners 46) to the landing zone area or landing zone material 44 on a garment-facing portion of the front waist region 12 of the absorbent article 10. The absorbent article 10 may also have front ears 47 in the front waist region 12. The absorbent article 10 may have a central lateral (or transverse) axis 48 and a central longitudinal axis 50. The central lateral axis 48 extends perpendicular to the central longitudinal axis 50.

Figure 4:
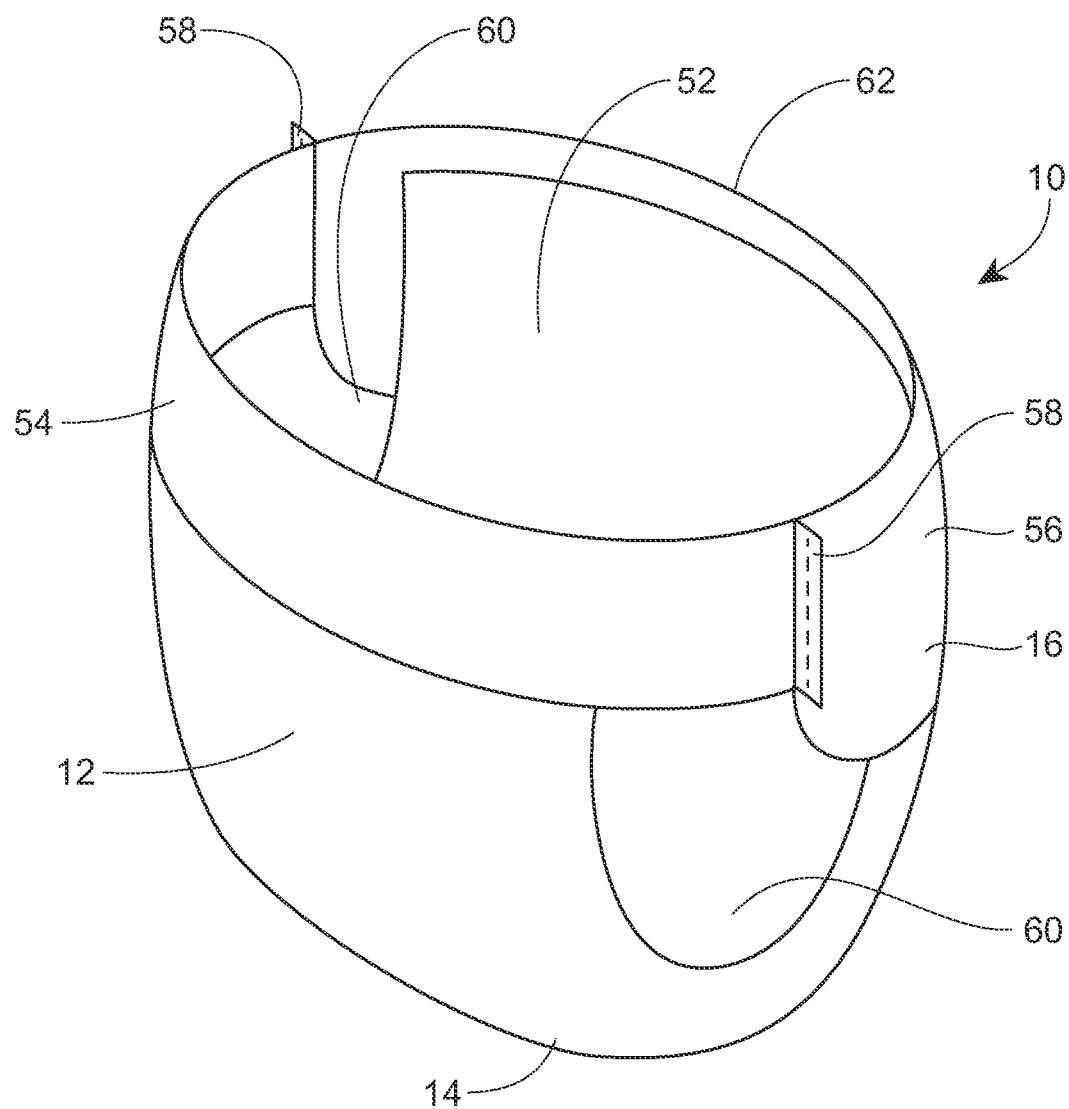
FIG. 4 is a front perspective view of an absorbent article in the form of a pant.
Figure 5:
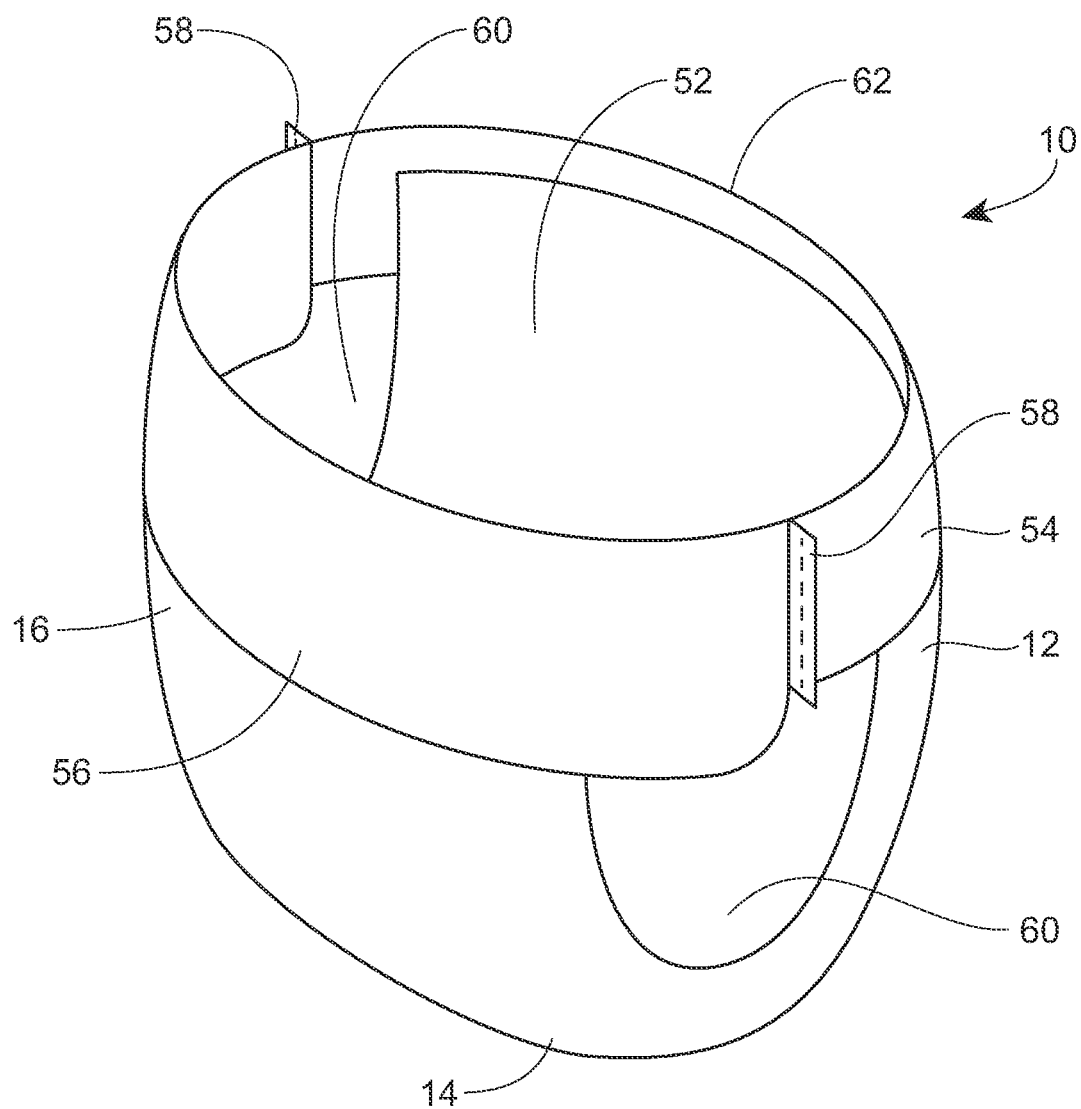
FIG. 5 is a rear perspective view of the absorbent article of FIG. 4.
Figure 6:
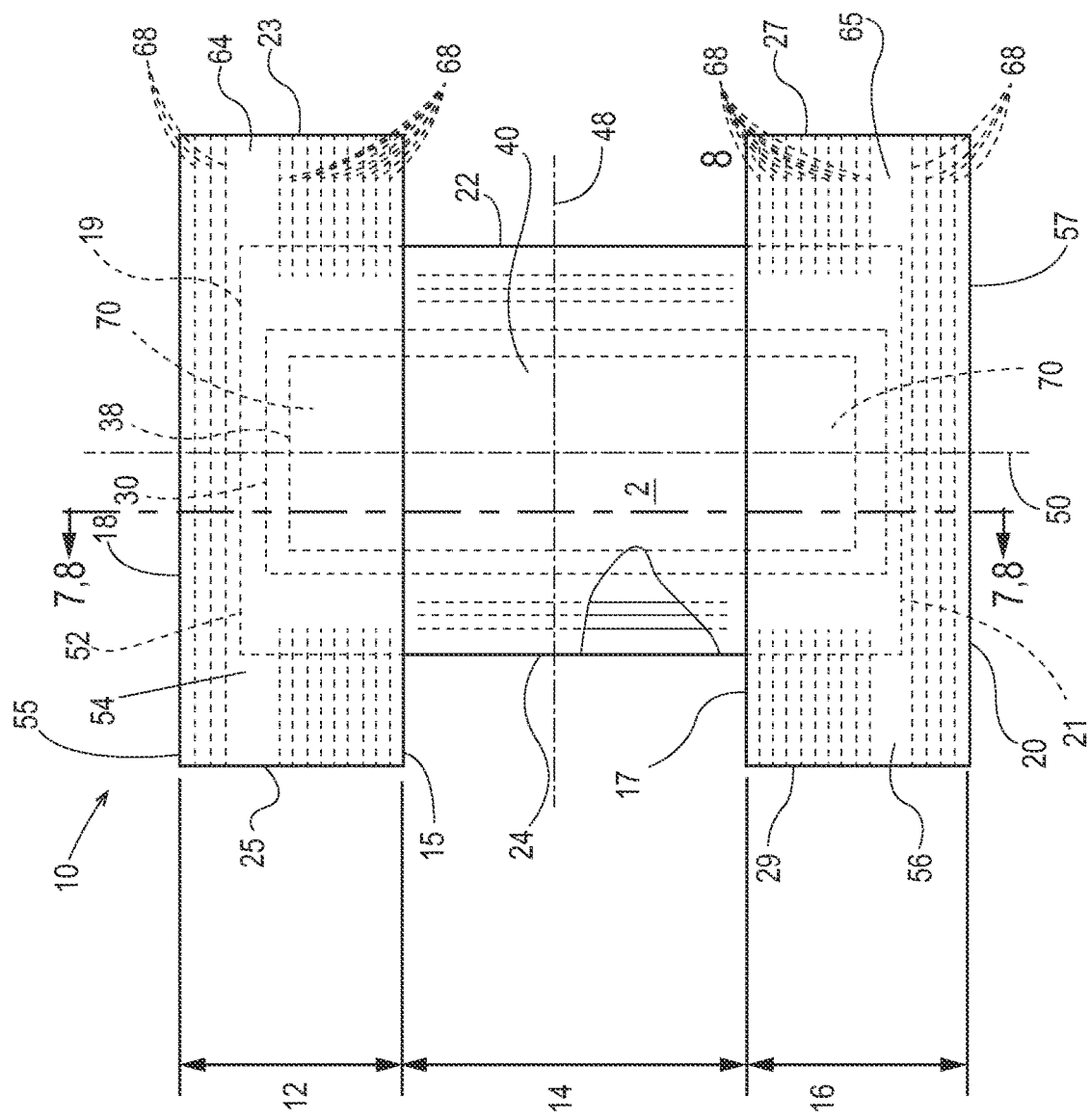
FIG. 6 is a plan view of the absorbent article of FIG. 4, laid flat, with a garment-facing surface facing the viewer.
Figure 7:
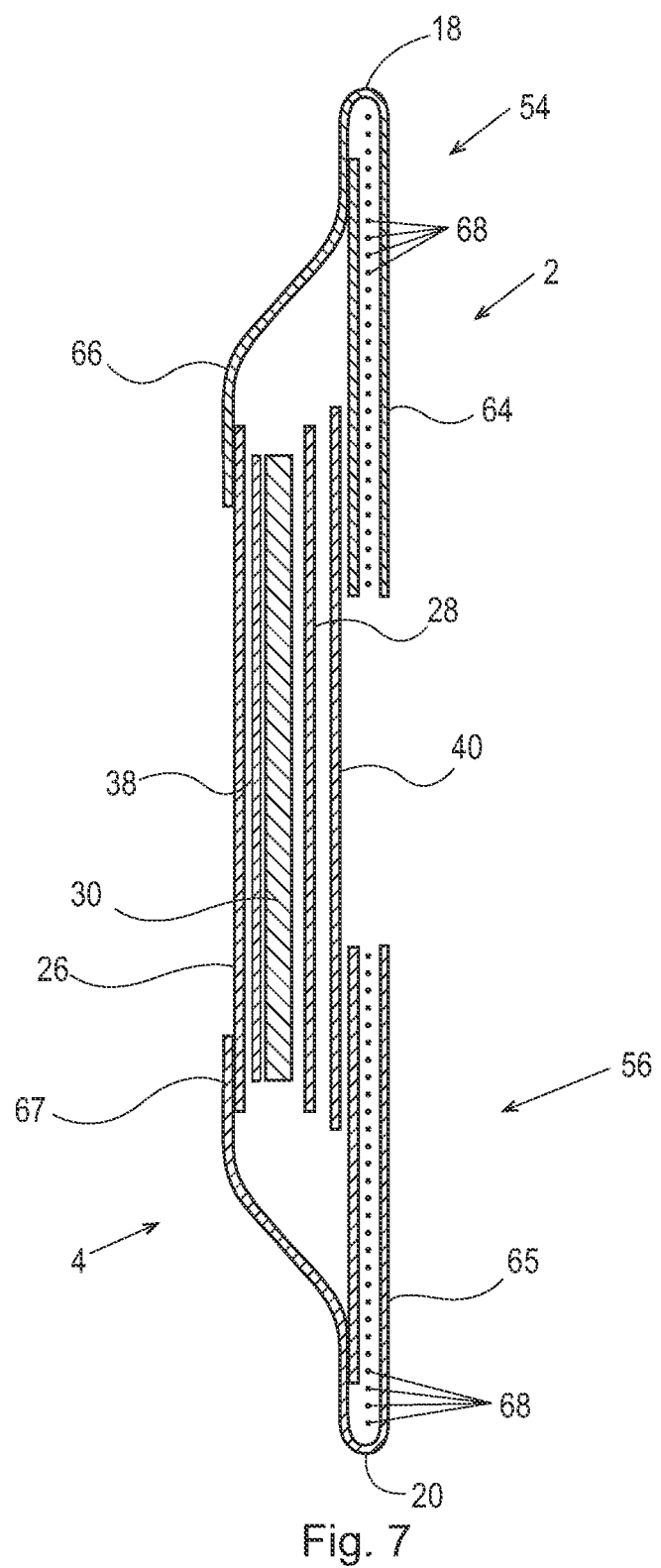
FIG. 7 is a cross-sectional view of the absorbent article taken about line 7-7 of FIG. 6.
Figure 8:
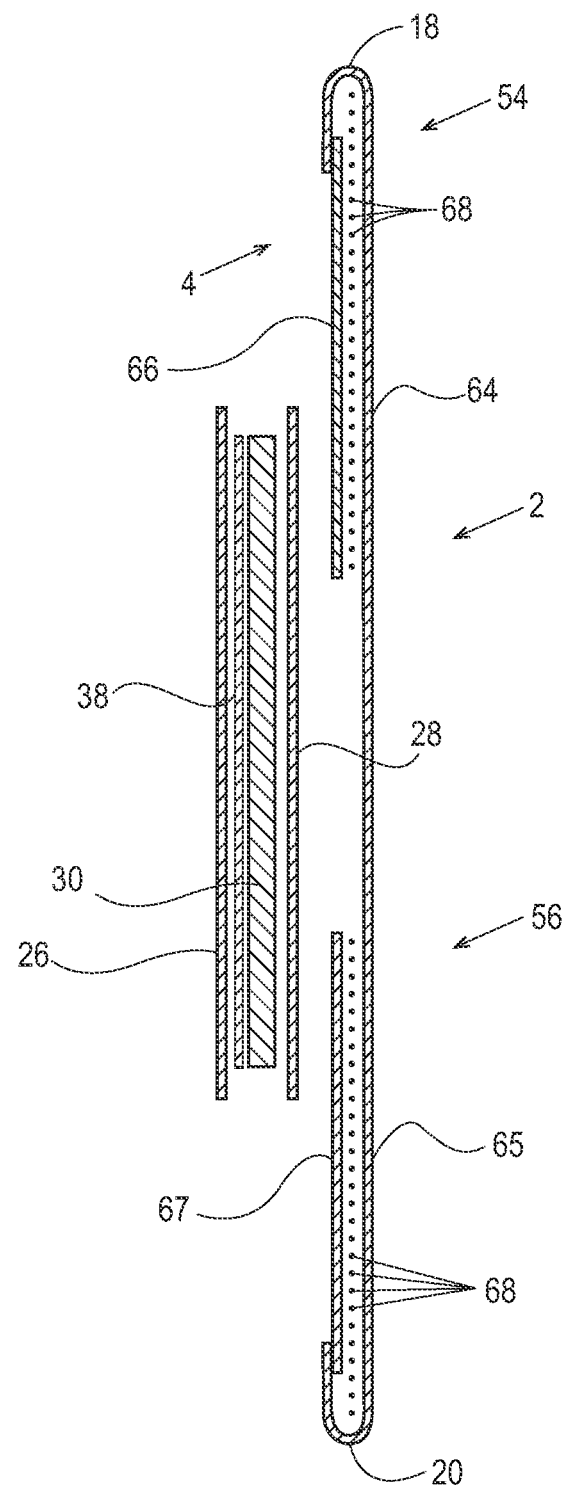
FIG. 8 is a cross-sectional view of the absorbent article taken about line 8-8 of FIG. 6.

In other instances, the absorbent article may be in the form of a pant having permanent or refastenable side seams. Suitable refastenable seams are disclosed in U.S. Pat. Appl. Pub. No. 2014/0005020 and U.S. Pat. No. 9,421,137. Referring to FIGS. 4-8, an example absorbent article 10 in the form of a pant is illustrated. FIG. 4 is a front perspective view of the absorbent article 10. FIG. 5 is a rear perspective view of the absorbent article 10. FIG. 6 is a plan view of the absorbent article 10, laid flat, with the garment-facing surface facing the viewer. Elements of FIG. 4-8 having the same reference number as described above with respect to FIGS. 1-3 may be the same element (e.g., absorbent core 30). FIG. 7 is an example cross-sectional view of the absorbent article taken about line 7-7 of FIG. 6. FIG. 8 is an example cross-sectional view of the absorbent article taken about line 8-8 of FIG. 6. FIGS. 7 and 8 illustrate example forms of front and back belts 54, 56. The absorbent article 10 may have a front waist region 12, a crotch region 14, and a back waist region 16. Each of the regions 12, 14, and 16 may be ⅓ of the length of the absorbent article 10. The absorbent article 10 may have a chassis 52 (sometimes referred to as a central chassis or central panel) comprising a topsheet 26, a backsheet 28, and an absorbent core 30 disposed at least partially intermediate the topsheet 26 and the backsheet 28, and an optional acquisition material 38, similar to that as described above with respect to FIGS. 1-3. The absorbent article 10 may comprise a front belt 54 in the front waist region 12 and a back belt 56 in the back waist region 16. The chassis 52 may be joined to a wearer-facing surface 4 of the front and back belts 54, 56 or to a garment-facing surface 2 of the belts 54, 56. Side edges 23 and 25 of the front belt 54 may be joined to side edges 27 and 29, respectively, of the back belt 56 to form two side seams 58. The side seams 58 may be any suitable seams known to those of skill in the art, such as butt seams or overlap seams, for example. When the side seams 58 are permanently formed or refastenably closed, the absorbent article 10 in the form of a pant has two leg openings 60 and a waist opening circumference 62. The side seams 58 may be permanently joined using adhesives or bonds, for example, or may be refastenably closed using hook and loop fasteners, for example.

The absorbent article 10 comprises a first nonwoven material, a second nonwoven material, and a bond area. The bond area comprises a portion of the first nonwoven material, a portion of the second nonwoven material, and a polymeric filler composition. The first nonwoven material and/or the second nonwoven material can be selected from the group consisting of a liquid permeable topsheet 26, a liquid impermeable backsheet 28, a barrier leg cuff material 32, nonwovens of elastic components, nonwoven stretch components, fastening materials, a front belt 54, a back belt 56, an acquisition material 38, a secondary top sheet 119, absorbent core 118 construction layers such as dusting layers and/or core covers, other nonwoven materials, and combinations thereof.

Belts

Referring to FIGS. 7 and 8, the front and back belts 54 and 56 may comprise front and back inner belt layers 66 and 67 and front and back outer belt layers 64 and 65 having an elastomeric material (e.g., strands 68 or a film (which may be apertured)) disposed at least partially therebetween. The elastic elements 68 or the film may be relaxed (including being cut) to reduce elastic strain over the absorbent core 30 or, may alternatively, run continuously across the absorbent core 30. The elastics elements 68 may have uniform or variable spacing therebetween in any portion of the belts. The elastic elements 68 may also be pre-strained the same amount or different amounts. The front and/or back belts 54 and 56 may have one or more elastic element free zones 70 where the chassis 52 overlaps the belts 54, 56. In other instances, at least some of the elastic elements 68 may extend continuously across the chassis 52.

The front and back inner belt layers 66, 67 and the front and back outer belt layers 64, 65 may be joined using adhesives, heat bonds, pressure bonds or thermoplastic bonds. Various suitable belt layer configurations can be found in U.S. Pat. Appl. Pub. No. 2013/0211363.

Front and back belt end edges 55 and 57 may extend longitudinally beyond the front and back chassis end edges 19 and 21 (as shown in FIG. 6) or they may be co-terminus. The front and back belt side edges 23, 25, 27, and 29 may extend laterally beyond the chassis side edges 22 and 24. The front and back belts 54 and 56 may be continuous (i.e., having at least one layer that is continuous) from belt side edge to belt side edge (e.g., the transverse distances from 23 to 25 and from 27 to 29). Alternatively, the front and back belts 54 and 56 may be discontinuous from belt side edge to belt side edge (e.g., the transverse distances from 23 to 25 and 27 to 29), such that they are discrete.

As disclosed in U.S. Pat. No. 7,901,393, the longitudinal length (along the central longitudinal axis 50) of the back belt 56 may be greater than the longitudinal length of the front belt 54, and this may be particularly useful for increased buttocks coverage when the back belt 56 has a greater longitudinal length versus the front belt 54 adjacent to or immediately adjacent to the side seams 58.

The front outer belt layer 64 and the back outer belt layer 65 may be separated from each other, such that the layers are discrete or, alternatively, these layers may be continuous, such that a layer runs continuously from the front belt end edge 55 to the back belt end edge 57. This may also be true for the front and back inner belt layers 66 and 67—that is, they may also be longitudinally discrete or continuous. Further, the front and back outer belt layers 64 and 65 may be longitudinally continuous while the front and back inner belt layers 66 and 67 are longitudinally discrete, such that a gap is formed between them—a gap between the front and back inner and outer belt layers 64, 65, 66, and 67 is shown in FIG. 7 and a gap between the front and back inner belt layers 66 and 67 is shown in FIG. 8.

The front and back belts 54 and 56 may include slits, holes, and/or perforations providing increased breathability, softness, and a garment-like texture. Underwear-like appearance can be enhanced by substantially aligning the waist and leg edges at the side seams 58 (see FIGS. 4 and 5).

The front and back belts 54 and 56 may comprise graphics (see e.g., 78 of FIG. 1). The graphics may extend substantially around the entire circumference of the absorbent article 10 and may be disposed across side seams 58 and/or across proximal front and back belt seams 15 and 17; or, alternatively, adjacent to the seams 58, 15, and 17 in the manner described in U.S. Pat. No. 9,498,389 to create a more underwear-like article. The graphics may also be discontinuous.

Alternatively, instead of attaching belts 54 and 56 to the chassis 52 to form a pant, discrete side panels may be attached to side edges of the chassis 22 and 24. Suitable forms of pants comprising discrete side panels are disclosed in U.S. Pat. Nos. 6,645,190; 8,747,379; 8,372,052; 8,361,048; 6,761,711; 6,817,994; 8,007,485; 7,862,550; 6,969,377; 7,497,851; 6,849,067; 6,893,426; 6,953,452; 6,840,928; 8,579,876; 7,682,349; 7,156,833; and 7,201,744.

Topsheet

The topsheet 26 is the part of the absorbent article 10 that is in contact with the wearer's skin. The topsheet 26 may be joined to portions of the backsheet 28, the absorbent core 30, the barrier leg cuffs 32, and/or any other layers as is known to those of ordinary skill in the art. The topsheet 26 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured (FIG. 2, element 31), may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson, et al., issued on May 13, 1997 and disclosed in U.S. Pat. Appl. Publication No. 2016/0136014 to Arora, et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

Backsheet

The backsheet 28 is generally that portion of the absorbent article 10 positioned proximate to the garment-facing surface of the absorbent core 30. The backsheet 28 may be joined to portions of the topsheet 26, the outer cover material 40, the absorbent core 30, and/or any other layers of the absorbent article by any attachment methods known to those of skill in the art. The backsheet 28 prevents, or at least inhibits, the bodily exudates absorbed and contained in the absorbent core 10 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

Outer Cover Material

The outer cover material (sometimes referred to as a backsheet nonwoven) 40 may comprise one or more nonwoven materials joined to the backsheet 28 and that covers the backsheet 28. The outer cover material 40 forms at least a portion of the garment-facing surface 2 of the absorbent article 10 and effectively "covers" the backsheet 28 so that film is not present on the garment-facing surface 2. The outer cover material 40 may comprise a bond pattern, apertures, and/or three-dimensional features.

Absorbent Core

Figure 9:
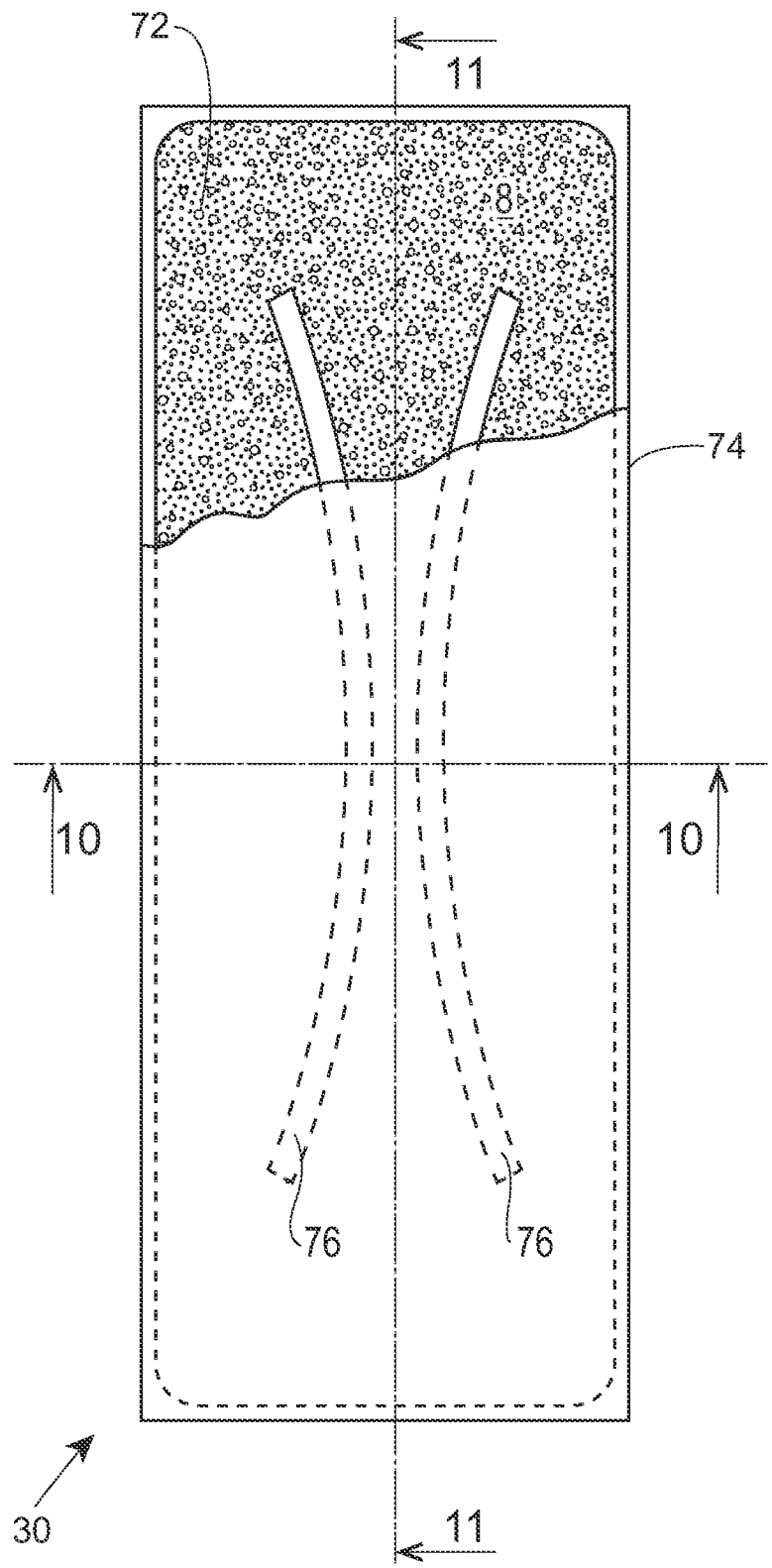
FIG. 9 is a plan view of an example absorbent core or an absorbent article.
Figure 10:
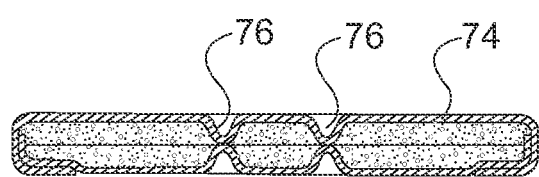
FIG. 10 is a cross-sectional view, taken about line 10-10, of the absorbent core of FIG. 9.
Figure 11:
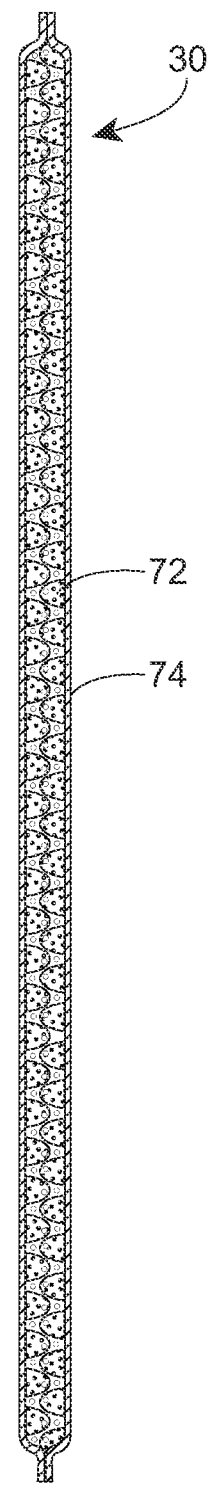
FIG. 11 is a cross-sectional view, taken about line 11-11, of the absorbent core of FIG. 10.

As used herein, the term "absorbent core" 30 refers to the component of the absorbent article 10 having the most absorbent capacity and that comprises an absorbent material. Referring to FIGS. 9-11, in some instances, absorbent material 72 may be positioned within a core bag or a core wrap 74. The absorbent material may be profiled or not profiled, depending on the specific absorbent article. The absorbent core 30 may comprise, consist essentially of, or consist of, a core wrap, absorbent material 72, and glue enclosed within the core wrap. The absorbent material may comprise superabsorbent polymers, a mixture of superabsorbent polymers and air felt, only air felt, and/or a high internal phase emulsion foam. In some instances, the absorbent material may comprise at least 80%, at least 85%, at least 90%, at least 95%, at least 99%, or up to 100% superabsorbent polymers, by weight of the absorbent material. In such instances, the absorbent material may be free of air felt, or at least mostly free of air felt. The absorbent core periphery, which may be the periphery of the core wrap, may define any suitable shape, such as rectangular "T," "Y," "hour-glass," or "dog-bone" shaped, for example. An absorbent core periphery having a generally "dog bone" or "hour-glass" shape may taper along its width towards the crotch region 14 of the absorbent article 10.

Referring to FIGS. 9-11, the absorbent core 30 may have areas having little or no absorbent material 72, where a wearer-facing surface of the core bag 74 may be joined to a garment-facing surface of the core bag 74. These areas having little or no absorbent material and may be referred to as "channels" 76. These channels can embody any suitable shapes and any suitable number of channels may be provided. In other instances, the absorbent core may be embossed to create the impression of channels. The absorbent core in FIGS. 9-11 is merely an example absorbent core. Many other absorbent cores with or without channels are also within the scope of the present disclosure.

Barrier Leg Cuffs/Leg Elastics

Referring to FIGS. 1 and 2, for example, the absorbent article 10 may comprise one or more pairs of barrier leg cuffs 32 and one or more pairs of leg elastics 34. The barrier leg cuffs 32 may be positioned laterally inboard of leg elastics 34. Each barrier leg cuff 32 may be formed by a piece of material which is bonded to the absorbent article 10 so it can extend upwards from a wearer-facing surface 4 of the absorbent article 10 and provide improved containment of body exudates approximately at the junction of the torso and legs of the wearer. The barrier leg cuffs 32 are delimited by a proximal edge joined directly or indirectly to the topsheet and/or the backsheet and a free terminal edge, which is intended to contact and form a seal with the wearer's skin. The barrier leg cuffs 32 may extend at least partially between the front end edge 18 and the back end edge 20 of the absorbent article 10 on opposite sides of the central longitudinal axis 50 and may be at least present in the crotch region 14. The barrier leg cuffs 32 may each comprise one or more elastics 33 (e.g., elastic strands or strips) near or at the free terminal edge. These elastics 33 cause the barrier leg cuffs 32 to help form a seal around the legs and torso of a wearer. The leg elastics 34 extend at least partially between the front end edge 18 and the back end edge 20. The leg elastics 34 essentially cause portions of the absorbent article 10 proximate to the chassis side edges 22, 24 to help form a seal around the legs of the wearer. The leg elastics 34 may extend at least within the crotch region 14.

Elastic Waistband

Referring to FIGS. 1 and 2, the absorbent article 10 may comprise one or more elastic waistbands 36. The elastic waistbands 36 may be positioned on the garment-facing surface 2 or the wearer-facing surface 4. As an example, a first elastic waistband 36 may be present in the front waist region 12 near the front belt end edge 18 and a second elastic waistband 36 may be present in the back waist region 16 near the back end edge 20. The elastic waistbands 36 may aid in sealing the absorbent article 10 around a waist of a wearer and at least inhibiting bodily exudates from escaping the absorbent article 10 through the waist opening circumference. In some instances, an elastic waistband may fully surround the waist opening circumference of an absorbent article.

Acquisition Materials

Referring to FIGS. 1, 2, 7, and 8, one or more acquisition materials 38 may be present at least partially intermediate the topsheet 26 and the absorbent core 30. The acquisition materials 38 are typically hydrophilic materials that provide significant wicking of bodily exudates. These materials may dewater the topsheet 26 and quickly move bodily exudates into the absorbent core 30. The acquisition materials 38 may comprise one or more nonwoven materials, foams, cellulosic materials, cross-linked cellulosic materials, air laid cellulosic nonwoven materials, spunlace materials, or combinations thereof, for example. In some instances, portions of the acquisition materials 38 may extend through portions of the topsheet 26, portions of the topsheet 26 may extend through portions of the acquisition materials 38, and/or the topsheet 26 may be nested with the acquisition materials 38. Typically, an acquisition material 38 may have a width and length that are smaller than the width and length of the topsheet 26. The acquisition material may be a secondary topsheet in the feminine pad context. The acquisition material may have one or more channels as described above with reference to the absorbent core 30 (including the embossed version). The channels in the acquisition material may align or not align with channels in the absorbent core 30. In an example, a first acquisition material may comprise a nonwoven material and as second acquisition material may comprise a cross-linked cellulosic material.

Landing Zone

Referring to FIGS. 1 and 2, the absorbent article 10 may have a landing zone area 44 that is formed in a portion of the garment-facing surface 2 of the outer cover material 40. The landing zone area 44 may be in the back waist region 16 if the absorbent article 10 fastens from front to back or may be in the front waist region 12 if the absorbent article 10 fastens back to front. In some instances, the landing zone 44 may be or may comprise one or more discrete nonwoven materials that are attached to a portion of the outer cover material 40 in the front waist region 12 or the back waist region 16 depending upon whether the absorbent article fastens in the front or the back. In essence, the landing zone 44 is configured to receive the fasteners 46 and may comprise, for example, a plurality of loops configured to be engaged with, a plurality of hooks on the fasteners 46, or vice versa.

Wetness Indicator/Graphics

Referring to FIG. 1, the absorbent articles 10 of the present disclosure may comprise graphics 78 and/or wetness indicators 80 that are visible from the garment-facing surface 2. The graphics 78 may be printed on the landing zone 40, the backsheet 28, and/or at other locations. The wetness indicators 80 are typically applied to the absorbent core facing side of the backsheet 28, so that they can be contacted by bodily exudates within the absorbent core 30. In some instances, the wetness indicators 80 may form portions of the graphics 78. For example, a wetness indicator may appear or disappear and create/remove a character within some graphics. In other instances, the wetness indicators 80 may coordinate (e.g., same design, same pattern, same color) or not coordinate with the graphics 78.

Front and Back Ears

Referring to FIGS. 1 and 2, as referenced above, the absorbent article 10 may have front and/or back ears 47, 42 in a taped diaper context. Only one set of ears may be required in most taped diapers. The single set of ears may comprise fasteners 46 configured to engage the landing zone or landing zone area 44. If two sets of ears are provided, in most instances, only one set of the ears may have fasteners 46, with the other set being free of fasteners. The ears, or portions thereof, may be elastic or may have elastic panels. In an example, an elastic film or elastic strands may be positioned intermediate a first nonwoven material and a second nonwoven material. The elastic film may or may not be apertured. The ears may be shaped. The ears may be integral (e.g., extension of the outer cover material 40, the backsheet 28, and/or the topsheet 26) or may be discrete components attached to a chassis 52 of the absorbent article on a wearer-facing surface 4, on the garment-facing surface 2, or intermediate the two surfaces 4, 2.

Sensors

Referring again to FIG. 1, the absorbent articles of the present disclosure may comprise a sensor system 82 for monitoring changes within the absorbent article 10. The sensor system 82 may be discrete from or integral with the absorbent article 10. The absorbent article 10 may comprise sensors that can sense various aspects of the absorbent article 10 associated with insults of bodily exudates such as urine and/or BM (e.g., the sensor system 82 may sense variations in temperature, humidity, presence of ammonia or urea, various vapor components of the exudates (urine and feces), changes in moisture vapor transmission through the absorbent articles garment-facing layer, changes in translucence of the garment-facing layer, and/or color changes through the garment-facing layer). Additionally, the sensor system 82 may sense components of urine, such as ammonia or urea and/or byproducts resulting from reactions of these components with the absorbent article 10. The sensor system 82 may sense byproducts that are produced when urine mixes with other components of the absorbent article 10 (e.g., adhesives, agm). The components or byproducts being sensed may be present as vapors that may pass through the garment-facing layer. It may also be desirable to place reactants in the absorbent article that change state (e.g. color, temperature) or create a measurable byproduct when mixed with urine or BM. The sensor system 82 may also sense changes in pH, pressure, odor, the presence of gas, blood, a chemical marker or a biological marker or combinations thereof. The sensor system 82 may have a component on or proximate to the absorbent article that transmits a signal to a receiver more distal from the absorbent article, such as an iPhone, for example. The receiver may output a result to communicate to the caregiver a condition of the absorbent article 10. In other instances, a receiver may not be provided, but instead the condition of the absorbent article 10 may be visually or audibly apparent from the sensor on the absorbent article.

Packages

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Arrays

"Array" means a display of packages comprising disposable absorbent articles of different article constructions (e.g., different elastomeric materials [compositionally and/or structurally] in the side panels, side flaps and/or belts flaps, different graphic elements, different product structures, fasteners or lack thereof). The packages may have the same brand and/or sub-brand and/or the same trademark registration and/or having been manufactured by or for a common manufacturer and the packages may be available at a common point of sale (e.g. oriented in proximity to each other in a given area of a retail store). An array is marketed as a line-up of products normally having like packaging elements (e.g., packaging material type, film, paper, dominant color, design theme, etc.) that convey to consumers that the different individual packages are part of a larger line-up. Arrays often have the same brand, for example, "Huggies," and same sub-brand, for example, "Pull-Ups." A different product in the array may have the same brand "Huggies" and the sub-brand "Little Movers." The differences between the "Pull-Ups" product of the array and the "Little Movers" product in the array may include product form, application style, different fastening designs or other structural elements intended to address the differences in physiological or psychological development. Furthermore, the packaging is distinctly different in that "Pull-Ups" is packaged in a predominately blue or pink film bag and "Little Movers" is packaged in a predominately red film bag.

Further regarding "Arrays," as another example an array may be formed by different products having different product forms manufactured by the same manufacturer, for example, "Kimberly-Clark", and bearing a common trademark registration for example, one product may have the brand name "Huggies," and sub-brand, for example, "Pull-Ups." A different product in the array may have a brand/sub-brand "Good Nites" and both are registered trademarks of The Kimberly-Clark Corporation and/or are manufactured by Kimberly-Clark. Arrays also often have the same trademarks, including trademarks of the brand, sub-brand, and/or features and/or benefits across the line-up. "On-line Array" means an "Array" distributed by a common on-line source.

Sanitary Napkin

Referring to FIG. 12, an absorbent article of the present disclosure may be a sanitary napkin 110. The sanitary napkin 110 may comprise a liquid permeable topsheet 114, a liquid impermeable, or substantially liquid impermeable, backsheet 116, and an absorbent core 118. The liquid impermeable backsheet 116 may or may not be vapor permeable. The absorbent core 118 may have any or all of the features described herein with respect to the absorbent core 30 and, in some forms, may have a secondary topsheet 119 (STS) instead of the acquisition materials disclosed above. The STS 119 may comprise one or more channels, as described above (including the embossed version). In some forms, channels in the STS 119 may be aligned with channels in the absorbent core 118. The sanitary napkin 110 may also comprise wings 120 extending outwardly with respect to a longitudinal axis 180 of the sanitary napkin 110. The sanitary napkin 110 may also comprise a lateral axis 190. The wings 120 may be joined to the topsheet 114, the backsheet 116, and/or the absorbent core 118. The sanitary napkin 110 may also comprise a front edge 122, a back edge 124 longitudinally opposing the front edge 122, a first side edge 126, and a second side edge 128 longitudinally opposing the first side edge 126. The longitudinal axis 180 may extend from a midpoint of the front edge 122 to a midpoint of the back edge 124. The lateral axis 190 may extend from a midpoint of the first side edge 128 to a midpoint of the second side edge 128. The sanitary napkin 110 may also be provided with additional features commonly found in sanitary napkins as is known in the art.

Examples Cross-Sections of Absorbent Articles

FIGS. 13-15 illustrate example cross-sectional views of absorbent articles within the scope of the present disclosure. FIG. 13 is an example cross-sectional view taken within a front waist region 12 of an absorbent article. FIG. 14 is an example cross-sectional view taken within a crotch region 14 of an absorbent article. FIG. 15 is an example cross-sectional view taken within a back waist region 16 of an absorbent article. In FIGS. 13-15, an outer cover material is element 40, a liquid permeable topsheet is element 26, opacity patches are elements 84, a liquid impermeable backsheet is element 28, an absorbent core is element 30, with the core bag being element 74, an absorbent material is element 72, and a distribution material is element 86. The distribution material 86 may comprise cross-linked cellulosic material and may be optional. An acquisition material is element 88. A liquid permeable topsheet is element 26. Barrier leg cuffs are elements 90. Elastics in the barrier leg cuffs are elements 92. Back ears are elements 42. Fasteners on the back ears 42 are elements 46. Construction glues and/or bonds between the various layers and/or components have been removed for clarity. Other cross-sectional configurations known to those of skill in the art are also within the scope of the present disclosure.

Bio-Based Content for Components

Components of the absorbent articles described herein may at least partially be comprised of bio-based content as described in U.S. Pat. Appl. No. 2007/0219521 A1. For example, the superabsorbent polymer component may be bio-based via their derivation from bio-based acrylic acid. Bio-based acrylic acid and methods of production are further described in U.S. Pat. Appl. Pub. No. 2007/0219521 and U.S. Pat. Nos. 8,703,450; 9,630,901 and 9,822,197. Other components, for example nonwoven and film components, may comprise bio-based polyolefin materials. Bio-based polyolefins are further discussed in U.S. Pat. Appl. Pub. Nos. 2011/0139657, 2011/0139658, 2011/0152812, and 2016/0206774, and U.S. Pat. No. 9,169,366. Example bio-based polyolefins for use in the present disclosure comprise polymers available under the designations SHA7260™, SHE150™, or SGM9450F™ (all available from Braskem S.A.).

An absorbent article component may comprise a bio-based content value from about 10% to about 100%, from about 25% to about 100%, from about 40% to about 100%, from about 50% to about 100%, from about 75% to about 100%, or from about 90% to about 100%, for example, using ASTM D6866-10, method B.

Recycle Friendly and Bio-Based Absorbent Articles

Components of the absorbent articles described herein may be recycled for other uses, whether they are formed, at least in part, from recyclable materials. Examples of absorbent article materials that may be recycled are nonwovens, films, fluff pulp, and superabsorbent polymers. The recycling process may use an autoclave for sterilizing the absorbent articles, after which the absorbent articles may be shredded and separated into different byproduct streams. Example byproduct streams may comprise plastic, superabsorbent polymer, and cellulose fiber, such as pulp. These byproduct streams may be used in the production of fertilizers, plastic articles of manufacture, paper products, viscose, construction materials, absorbent pads for pets or on hospital beds, and/or for other uses. Further details regarding absorbent articles that aid in recycling, designs of recycle friendly diapers, and designs of recycle friendly and bio-based component diapers, are disclosed in U.S. Provisional Pat. Appl. No. 62/597,539, P&G Docket Number 15058P, filed on Dec. 12, 2017.

General Description of Polymeric Filler Compositions and Comparative Tackified Adhesive Compositions Described herein is a polymeric filler composition comprising at least 50%, alternatively from about 98% to about 98.5%, alternatively at least 75%, alternatively at least 85%, alternatively at least 90%, alternatively at least 95%, alternatively at least 98%, alternatively at least 99%, and alternatively 100% of a polymer, by weight of the polymeric filler composition. The polymer may be a copolymer or a homopolymer. The polymer may be an amorphous poly alpha olefin.

The polymer can comprise 100%, alternatively from about 75% to about 95%, alternatively from about 80% to about 90%, alternatively from about 30% to about 70%, alternatively from about 35% to about 65%, alternatively from about 40% to about 60%, alternatively from about 45% to about 55%, alternatively from about 10% to about 20%, alternatively from about 15% to about 25%, alternatively from about 1% to about 5%, and alternatively from about 5% to about 12% of propene monomer units, by weight of the polymer. The percentage of propene monomer units may be determined by a suitable method, such as nuclear magnetic resonance or infrared spectroscopies, known to those of skill in the art.

The polymer can comprise 100%, alternatively from about 75% to about 95%, alternatively from about 80% to about 90%, alternatively from about 30% to about 70%, alternatively from about 35% to about 65%, alternatively from about 40% to about 60%, alternatively from about 45% to about 55%, alternatively from about 10% to about 20%, and alternatively from about 15% to about 25%, alternatively from about 1% to about 5%, and alternatively from about 5% to about 12% of ethylene monomer units, by weight of the polymer. The percentage of ethylene monomer units may be determined by a suitable method, such as nuclear magnetic resonance or infrared spectroscopies, known to those of skill in the art.

The polymer can comprise 100%, alternatively from about 75% to about 95%, alternatively from about 80% to about 90%, alternatively from about 30% to about 70%, alternatively from about 35% to about 65%, alternatively from about 40% to about 60%, alternatively from about 45% to about 55%, alternatively from about 10% to about 20%, and alternatively from about 15% to about 25%, alternatively from about 1% to about 5%, and alternatively from about 5% to about 12% of 1-butene monomer units, by weight of the polymer. The percentage of 1-butene monomer units may be determined by a suitable method, such as nuclear magnetic resonance or infrared spectroscopies, known to those of skill in the art.

If the polymer is a copolymer, it can comprise from about 1% to about 40%, alternatively from about 2% to about 30%, alternatively from about 5% to about 20%, and alternatively from about 10% to about 15%, by weight of the copolymer, of one or more comonomer units selected from the group consisting of 4-methyl-1-pentene, pentene-1, 2-methylpentene-1, 3-methylbutene-1, heptene-1, dimethylpentene-1, trimethylbutene-1, ethylpentene-1, methylpentene-1, trimethylpentene-1, methylethylpentene-1, 1-octene, diethylbutene-1, propylpentane-1, decene-1, methylnonene-1, nonene-1, trimethylheptene-1, methylethylbutene-1, dodecene-1, and hexadodecene-1, and combinations thereof.

The polymer can be prepared by the methods described in U.S. Pat. Nos. 5,302,675 and 5,723,546, which are both expressly incorporated herein. The polymer may be prepared using a single-site catalyst system, multiple single-site catalyst systems, or Ziegler Natta catalyst system. Monomers used to prepare the copolymer can be obtained from one or more carbon-based sources, e.g., biomass from animal and/or vegetable fats. The monomers can also be obtained from renewable feed stocks provided by, e.g., Neste's Rotterdam Refinery (Neste, Finland). Polymeric filler compositions comprising a polymer can be prepared by combining the polymer and at least one optional ingredient (e.g., an optical brightener, other copolymers), if desired. The polymer can be prepared into a final polymeric filler composition by heating the primary polymer to elevated temperatures (e.g., about 135 to about 175° C.) that melts the polymer. Once molten, one or more optional ingredients (e.g., additive or other polymers components) can be added to the primary polymer. A mixer can be used to mix the components together into a final polymeric filler composition.

The polymeric filler composition can comprise less than 5%, alternatively less than 3%, alternatively less than 2%, alternatively less than 1%, alternatively less than 0.5%, and alternatively less than 0.1% of a tackifier, by weight of the polymer filler composition. Exemplary tackifiers can include aliphatic hydrocarbon resins, aromatic modified aliphatic hydrocarbon resins, hydrogenated poly-cyclopentadiene resins, poly-cyclopentadiene resins, gum rosins, gum rosin esters, wood rosins, wood rosin esters, tall oil rosins, tall oil rosin esters, poly-terpenes, aromatic modified poly-terpenes, terpene-phenolics, aromatic modified hydrogenated poly-cyclopentadiene resins, hydrogenated aliphatic resins, hydrogenated aliphatic aromatic resins, hydrogenated terpenes and modified terpenes, and hydrogenated rosin esters.

The polymeric filler composition can be free of a tackifier. The polymeric filler composition may comprise 0% tackifier. There are significant advantages to minimizing or avoiding the use of a tackifier as it may reduce the cost of the polymeric filler composition, as well as eliminate an additional ingredient and potential issues that may be associated with supplying the additional ingredient. Furthermore, tackifiers may impart undesirable odor in disposable articles and can also act as carriers of low molecular weight plasticizers (e.g., process oils that are used in SBC based adhesives) that may weaken the polyethylene back sheet materials used in absorbent articles and textile articles.

The polymeric filler composition may comprise a homopolymer of propylene. The homopolymer or propylene may be made using one or more metallocene catalysts. The homopolymer of propylene may have low modulus compared to typical homopolymers of propylene due to less stereoregularity. The homopolymer or propylene may comprise 0% tackifier. The homopolymer or propylene may have a number average molecular weight of from about 20,000 g/mole to about 70,000 g/mole, alternatively from about 30,000 g/mole to about 60,000 g/mole, alternatively from about 40,000 g/mole to about 50,000 g/mole, and alternatively from about 43,000 g/mole to about 47,000 g/mole. The homopolymer or propylene may have a viscosity of from about 5,000 mPa·s to about 12,000 mPa·s, alternatively from about 7,000 mPa·s to about 10,000 mPa·s, alternatively from about 8,000 mPa·s to about 9,000 mPa·s, and alternatively about 8,500 mPa·s at 190° C. according to ASTM D3236-88. An example of a homopolymer or propylene may be L-Modu S410 from Idemitsu.

The polymeric filler composition may comprise an amorphous poly alpha olefin. The amorphous poly alpha olefin may be a copolymer comprising propylene and 1-butene. The amorphous poly alpha olefin may be produced using a Ziegler-Natta catalyst. The amorphous poly alpha olefin may comprise 0% tackifier. The amorphous poly alpha olefin may have a viscosity of about 3,000 mPa·s, alternatively from about 2,000 mPa·s to about 5,000 mPa·s, and alternatively from about 2,500 mPa·s to about 4,500 mPa·s at 190° C. according to ASTM D3236-88. An example of an amorphous poly alpha olefin may be RT2830 from REXtac.

The polymeric filler composition may comprise a copolymer comprising propylene and ethylene. The copolymer comprising propylene and ethylene may be made using one or more metallocene catalysts. The copolymer comprising propylene and ethylene may comprise 0% tackifier. The copolymer comprising propylene and ethylene may have a viscosity of about 3,000 mPa·s, alternatively from about 1,000 mPa·s to about 5,000 mPa·s, alternatively from about 1,500 mPa·s to about 4,000 mPa·s, alternatively from about 1,750 mPa·s to about 3,000 mPa·s, alternatively from about 2,000 mPa·s to about 2,500 mPa·s, alternatively from about 2,000 mPa·s to about 2,200 mPa·s, and alternatively about 2,100 mPa·s at 170° C. according to ASTM D3236-88. An example of a copolymer comprising propylene and ethylene may be Licocene 2502 from Clariant.

The polymeric filler composition may comprise a homopolymer of propylene. The homopolymer of propylene may comprise 0% tackifier. The homopolymer of propylene may have a viscosity of from about 500 mPa·s to about 3,000 mPa·s, alternatively from about 750 mPa·s to about 2,250 mPa·s, and alternatively from about 1,200 mPa·s to about 1,800 mPa·s at 170° C. according to ASTM D3236-88. The homopolymer of propylene may be made using one or more metallocene catalysts. An example of a homopolymer of propylene may be Licocene 6502 from Clariant.

A comparative tackified adhesive composition may be a styrenic block copolymer based adhesive comprising at least 20% of a tackifier, by weight of the tackified adhesive composition. The adhesive may have a viscosity of from about 2,000 mPa·s to about 7,000 mPa·s, alternatively from about 3,000 mPa·s to about 6,000 mPa·s, alternatively from about 4,000 mPa·s to about 5,500 mPa·s, and alternatively about 4,725 mPa·s at 160° C. according to ASTM D3236-88. An example of this adhesive may be H2401 from Bostik.

Another comparative tackified adhesive composition may be a polyolefin based adhesive comprising at least 20% of a tackifier, by weight of the tackified adhesive composition. The adhesive may have a viscosity of from about 3,000 mPa·s to about 9,000 mPa·s, alternatively from about 4,000 mPa·s to about 7,000 mPa·s, alternatively from about 5,000 mPa·s to about 6,500 mPa·s, alternatively from about 5,750 mPa·s to about 6,250 mPa·s, and alternatively about 6,000 mPa·s at 160° C. according to ASTM D3236-88. An example of this adhesive may be DM3800 from Henkel.

The polymeric filler composition may optionally comprise an antioxidant or a stabilizer. Any antioxidant known to a person of ordinary skill in the art may be used in the adhesion composition. Non-limiting examples of suitable antioxidants include amine-based antioxidants such as alkyl diphenyl amines, phenyl-naphthylamine, alkyl or aralkyl substituted phenyl-naphthylamine, alkylated p-phenylene diamines, tetramethyl-diaminodiphenylamine and the like; and hindered phenol compounds such as 2,6-di-t-butyl-4-methylphenol; 1,3,5-trimethyl-2,4,6-tris(3',5'-di-t-butyl-4'-hydroxybenzyl)benzene; tetra kis [(methylene(3,5-di-t-butyl-4-hydroxyhydrocinnamate)]methane (e.g., IRGANOX™ 1010, from Ciba Geigy, New York); octadecyl-3,5-di-t-butyl-4-hydroxycinnamate (e.g., IRGANOX™ 1076, commercially available from Ciba Geigy) and combinations thereof. When used, the amount of the antioxidant and/or the stabilizer in the polymeric filler composition can be less than 1%, alternatively from about 0.05% to about 0.75%, and alternatively from about 0.1% to about 0.5%, by weight of the polymeric filler composition.

The polymeric filler composition may optionally comprise a UV stabilizer that may prevent or reduce the degradation of the composition by radiation. Any UV stabilizer known to a person of ordinary skill in the art may be used in the polymeric filler composition. Non-limiting examples of suitable UV stabilizers include benzophenones, benzotriazoles, aryl esters, oxanilides, acrylic esters, formamidine carbon black, hindered amines, nickel quenchers, hindered amines, phenolic antioxidants, metallic salts, zinc compounds, and combinations thereof. Where used, the amount of the UV stabilizer in the polymeric filler composition can be less than 1%, alternatively from about 0.05% to about 0.75%, and alternatively from about 0.1% to about 0.5%, by weight of the polymeric filler composition The polymeric filler composition may optionally comprise a brightener, colorant, and/or pigment. Any colorant or pigment known to a person of ordinary skill in the art may be used in the polymeric filler composition. Non-limiting examples of suitable brighteners, colorants, and/or pigments include fluorescent materials and pigments such as triazine-stilbene, coumarin, imidazole, diazole, titanium dioxide and carbon black, phthalocyanine pigments, and other organic pigments such as IRGAZINB, CROMOPHTALB, MONASTRALB, CINQUASIAB, IRGALITEB, ORASOLB, all of which are available from Ciba Specialty Chemicals, Tarrytown, N.Y. Where used, the amount of the brightener, colorant, and/or pigment in the polymeric filler composition can be less than 10%, alternatively from about 0.01% to about 5%, and alternatively from about 0.1% to about 2%, by weight of the polymeric filler composition.

The polymeric filler composition may optionally comprise a fragrance such as a perfume or other odorant. Such fragrances may be retained by a liner or contained in release agents such as microcapsules that may, for example, release fragrance upon removal of a release liner from or compression on the adhesive composition. Where used, the amount of the fragrance in the polymeric filler composition can be less than 3%, alternatively less than 2%, alternatively less than 1%, alternatively from about 0.05% to about 0.75%, and alternatively from about 0.1% to about 0.5%, by weight of the polymeric filler composition The polymeric filler composition may have a Peak Peel Strength of from about 0.1 N/cm to about 9 N/cm, alternatively from about 0.15 N/cm to about 9 N/cm, alternatively from about 0.15 N/cm to about 1.0 N/cm, alternatively from about 0.1 N/cm to about 0.5 N/cm, alternatively from about 0.2 N/cm to about 0.4 N/cm, alternatively from about 0.2 N/cm to about 0.8 N/cm, alternatively from about 0.25 N/cm to about 0.71 N/cm, alternatively from about 1.15 N/cm to about 2 N/cm, alternatively from about 1.2 N/cm to about 1.8 N/cm, alternatively from about 1.22 N/cm to about 1.75 N/cm, alternatively from about 1.8 N/cm to about 3 N/cm, alternatively from about 1.85 N/cm to about 2.7 N/cm, alternatively from about 1.88 N/cm to about 2.62 N/cm, alternatively from about 0.4 N/cm to about 3.0 N/cm, alternatively from about 0.5 N/cm to about 2.5 N/cm, alternatively from about 0.6 N/cm to about 2.3 N/cm, alternatively from about 0.65 N/cm to about 2.22 N/cm, alternatively from about 1.75 N/cm to about 3.0 N/cm, alternatively from about 1.8 N/cm to about 2.3 N/cm, and alternatively from about 1.85 to about 2.22 after exposure to a skin-protecting material for 24 hours according to the Laminate Peel Test Method described herein.

The polymeric filler composition may have a Tensile Strength at Yield of from about 0.5 MPa to about 10 MPa, alternatively from about 1 MPa to about 8 MPa, alternatively from about 2 MPa to about 6 MPa, alternatively from about 4 MPa to about 7 MPa, alternatively from about 4.5 MPa to about 6 MPa, alternatively from about 4.94 MPa to about 5.76 MPa, alternatively from about 0.5 MPa to about 4.5 MPa, alternatively from about 1 MPa to about 4 MPa, alternatively from about 2 MPa to about 4 MPa, alternatively from about 2.06 MPa to about 3.53 MPa, and alternatively from about 0.5 MPa to about 7 MPa, according to the Tensile Strength Test Method described herein.

The polymeric filler composition may have a Modulus of Elasticity of from about 40 MPa to about 500 MPa, alternatively from about 50 MPa to about 300 MPa, alternatively from about 50 MPa to about 250 MPa, alternatively from about 52.1 MPa to about 235 MPa, alternatively from about 5 MPa to about 45 MPa, alternatively from about 10 MPa to about 30 MPa, alternatively from about 15 MPa to about 25 MPa, alternatively from about 19.4 MPa to about 20.6 MPa, and alternatively from about 5 MPa to about 400 MPa according to the Modulus of Elasticity Test Method described herein.

The bond area may comprise from about 13 gsm to about 30 gsm, alternatively from about 15 gsm to about 25 gsm, alternatively from about 7 gsm to about 13 gsm, alternatively from about 9 gsm to about 11 gsm, alternatively from about 5 gsm to about 30 gsm, alternatively from about 6 gsm to about 27 gsm, alternatively from about 10 gsm to about 25 gsm, alternatively from about 20 gsm to about 30 gsm, alternatively from about 23 gsm to about 27 gsm, alternatively about 10 gsm, alternatively about 15 gsm, and alternatively about 25 gsm of the polymeric filler composition disposed within the bond area.

General Description of Various Skin-Protecting Materials

A first skin-protecting material may comprise a mineral oil. The first skin-protecting material may be a paraffinic mineral oil. The first skin-protecting material may comprise a perfume. The first skin-protecting material may comprise from about 95 wt. % to 100 wt. % mineral oil, alternatively from about 97 wt. % to about 99.5 wt. % mineral oil, and alternatively from about 98 wt. % to about 99 wt. % mineral oil. The mineral oil may be any of various colorless, odorless, light mixtures of higher alkanes from a mineral source. The mineral oil may be a distillate of petroleum. The mineral oil may be selected from a white oil, a paraffin oil, a liquid paraffin, and mixtures thereof. An example of a product that may comprise the first skin-protecting material may be Johnson & Johnson Johnson's® Baby Oil sold by Johnson & Johnson.

A second skin-protecting material may comprise a petroleum based material selected from the group consisting of a petrolatum, a petroleum jelly, a white petrolatum, a soft petrolatum, a soft paraffin/paraffin wax, a multi-hydrocarbon, and mixtures thereof. The petroleum based material may be a semi-solid mixture of hydrocarbons, optionally with carbon numbers higher than 25. The petroleum based material may be USP grade suitable for medicinal and personal care applications. The second skin-protecting material may comprise a perfume. The second skin-protecting material may comprise from about 5 wt. % to about 50 wt. %, alternatively from about 10 wt. % to about 45 wt. %, alternatively from about 11 wt. % to about 15 wt. %, alternatively from about 20 wt. % to about 40 wt. %, alternatively from about 25 wt. % to about 25 wt. %, and alternatively from about 38 wt. % to about 42 wt. % zinc oxide.

The second skin-protecting material may comprise from about 10 wt. % to about 100 wt. %, alternatively from about 20% to about 99%, alternatively from about 30 wt. % to about 98 wt. %, alternatively from about 40 wt. % to about 97 wt. %, alternatively from about 50 wt. % to about 96 wt. %, alternatively from about 50 wt. % to about 95 wt. %, alternatively from about 60 wt. % to about 93 wt. %, alternatively from about 70 wt. % to about 91 wt. %, alternatively from about 80 wt. % to about 89 wt. %, and alternatively from about 83 wt. % to about 87 wt. % of the petroleum based material. The second skin-protecting material may further comprise beeswax, mineral oil, dimethicone, glycerine, perfume, and/or Aloe Barbadensis Leaf Extract. The second skin-protecting material may further comprise beeswax, cod liver oil, lanolin, talc, dimethicone, glycerine, and/or perfume. An example of a product that may comprise the second skin-protecting material may be Desitin® Rapid Relief Cream sold by Johnson & Johnson.

A third skin-protecting material may comprise a natural oil and/or natural extract. The third skin-protecting material may comprise ingredients selected from the group consisting of sweet almond oil and/or extract, calendula flower oil and/or extract, chamomile flower oil and/or extract, glycerol linoleate, wool wax, clay, lavender oil and/or extract, rosemary leaf oil and/or extract, sage oil and/or extract, sesame seed oil and/or extract, water, and mixtures thereof. The third skin-protecting material may comprise zinc oxide, coconut oil and/or extract, sweet almond oil and/or extract, sesame oil and/or extract, glycerin, wool wax, hydrolyzed beeswax, glycerol oleate, beeswax, Borago officinalis seed oil and/or extract, sunflower seed oil and/or extract, althaea officinalis root extract, viola tricolor extract, glyceryl caprylate, sodium lauroyl lactalate, lactate, water, and mixtures thereof. Examples of a product that may comprise the third skin-protecting material may be Calendula Diaper Rash Cream, Diaper Care Cream—White Mallow, both sold by Weleda.

The third skin-protecting material may comprise one or more natural oils, natural extracts, natural fats, and/or derivatives thereof. Non-limiting examples include oleic canola oil (Brassica campestris, B. napus, B. rapa; having an oleic content greater than 70%, e.g., high oleic canola oil, very high oleic canola oil, or partially hydrogenated canola oil), marula kernel oil, palm oil, palm olein, palm stearin, palm superolein, avocado oil, pecan oil, pumpkin seed oil, oleic safflower oil (having an oleic content of greater than 30% and omega-6 fatty acid content of less than 50%, e.g., high oleic safflower oil), sesame oil, soybean oil (e.g., high oleic soybean, low linolenic soybean oil, partially hydrogenated), oleic sunflower oil (having an oleic content of greater than 40%, e.g., mid oleic sunflower or high oleic sunflower oil), apricot oil, babassu oil, castor oil, coconut oil, cod liver oil, hydrogenated corn oil, hydrogenated cottonseed oil, hazelnut oil, jojoba oil, macadamia oil, meadowfoam seed oil, maringa oil, olive oil, marula oil, palm kernel oil, hydrogenated rapeseed oil, rose hip oil, hydrogenated safflower oil, hydrogenated soybean oil, hydrogenated sunflower oil, cocoa butter, hydrogenated walnut oil, hydrogenated wheat germ oil, flaxseed oil, argan oil, neem oil, saffron extract or essential oil, tea tree extract or essential oil, sandalwood extract or essential oil, frankincense extract or essential oil, myrrh extract or essential oil, clove extract or essential oil, niaouli extract or essential oil, peppermint extract or essential oil, eucalyptus extract or essential oil, Melrose extract or essential oil, or the hardened derivatives thereof.

The third skin-protecting material may comprise from about 10 wt. % to about 100 wt. %, alternatively from about 20% to about 99%, alternatively from about 30 wt. % to about 98 wt. %, alternatively from about 40 wt. % to about 97 wt. %, alternatively from about 50 wt. % to about 96 wt. %, alternatively from about 50 wt. % to about 95 wt. %, alternatively from about 60 wt. % to about 93 wt. %, alternatively from about 70 wt. % to about 91 wt. %, alternatively from about 80 wt. % to about 89 wt. %, and alternatively from about 83 wt. % to about 87 wt. % of the natural oil, natural extract, natural fat, and/or derivatives thereof.

Examples & Data

The following examples, comparative examples, and data are provided to help illustrate the polymeric filler compositions and bond areas described herein. The exemplified bond areas were prepared according to the Laminate Peel Test Method described herein. It will be appreciated that other modifications to the polymeric filler compositions described herein within the skill of those in the formulation art may be undertaken. All parts, percentages, and ratios herein are by weight unless otherwise specified.

TABLE 1

| Tensile Strength at Yield (MPa) | Modulus of Elasticity (MPa) | Polymeric Filler Composition | Peak Peel Strength (N/cm) 10 gsm | Peak Peel Strength (N/cm) 15 gsm | Peak Peel Strength (N/cm) 25 gsm |
|---|---|---|---|---|---|
| 5.76 | 52.1 | Licocene 2502[1] | 0.2 | 0.28 | 0.25 |
| 4.94 | 235 | Licocene 6502[2] | 0.39 | 0.54 | 0.71 |
| 3.53 | 20.6 | L-Modu S410[3] | 0 | 0 | 0 |
| 2.06 | 19.4 | REXtac RT-2830[4] | 0 | 0.1 | 0.19 |
| 0.02 | 0.138 | Bostik H2401[5] | 0 | 0 | 0 |
| 0.33 | 2.08 | Henkel DM3800[6] | 0 | 0 | 0 |

[1] Available from Clariant
[2] Available from Clariant
[3] Available from Idemitsu
[4] Available from REXtac LLC
[5] Available from Bostik
[6] Available from Henkel Table 1 provides measurements of the Peak Peal Strength for various bond areas comprising various polymeric filler compositions at various gsm amounts after exposure to Johnson & Johnson Johnson's® Baby Oil sold by Johnson & Johnson according to the Laminate Peel Test Method described herein. Table 1 also provides measurements of the Peak Peal Strength for various bond areas comprising various tackified adhesive compositions at various gsm amounts after exposure to Johnson & Johnson Johnson's® Baby Oil sold by Johnson & Johnson according to the Laminate Peel Test Method described herein. The Peak Peel Strength was measured according to the Laminate Peel Test Method described herein.

In addition, Table 1 provides measurements of the Tensile Strength at Yield, according to the Tensile Strength Test Method described herein, and the Modulus of Elasticity, according to the Modulus of Elasticity Test Method described herein for various bond areas comprising various polymeric filler compositions at various gsm amounts. Table 1 also provides measurements of the Tensile Strength at Yield, according to the Tensile Strength Test Method described herein, and the Modulus of Elasticity, according to the Modulus of Elasticity Test Method described herein for various bond areas comprising various tackified adhesive compositions at various gsm amounts.

TABLE 2

| Tensile Strength at Yield (MPa) | Modulus of Elasticity (MPa) | Polymeric Filler Composition | Peak Peel Strength (N/cm) 10 gsm | Peak Peel Strength (N/cm) 15 gsm | Peak Peel Strength (N/cm) 25 gsm |
|---|---|---|---|---|---|
| 5.76 | 52.1 | Licocene 2502[1] | 1.09 | 1.56 | 1.69 |
| 4.94 | 235 | Licocene 6502[2] | 0.75 | 1.03 | 1.32 |
| 3.53 | 20.6 | L-Modu S410[3] | 1.75 | 2.45 | 2.62 |
| 2.06 | 19.4 | REXtac RT-2830[4] | 1.22 | 1.88 | 2.1 |
| 0.02 | 0.138 | Bostik H2401[5] | 0 | 0.06 | 0.12 |
| 0.33 | 2.08 | Henkel DM3800[6] | 0.39 | 0.69 | 0.43 |

[1] Available from Clariant
[2] Available from Clariant
[3] Available from Idemitsu
[4] Available from REXtac LLC
[5] Available from Bostik
[6] Available from Henkel Table 2 provides measurements of the Peak Peal Strength for various bond areas comprising various polymeric filler compositions at various gsm amounts after exposure to Calendula Diaper Rash Cream sold by Weleda according to the Laminate Peel Test Method described herein. Table 2 also provides measurements of the Peak Peal Strength for various bond areas comprising various tackified adhesive compositions at various gsm amounts after exposure to Calendula Diaper Rash Cream sold by Weleda according to the Laminate Peel Test Method described herein. The Peak Peel Strength was measured according to the Laminate Peel Test Method described herein.

In addition, Table 2 provides measurements of the Tensile Strength at Yield, according to the Tensile Strength Test Method described herein, and the Modulus of Elasticity, according to the Modulus of Elasticity Test Method described herein for various bond areas comprising various polymeric filler compositions at various gsm amounts. Table 2 also provides measurements of the Tensile Strength at Yield, according to the Tensile Strength Test Method described herein, and the Modulus of Elasticity, according to the Modulus of Elasticity Test Method described herein for various bond areas comprising various tackified adhesive compositions at various gsm amounts.

TABLE 3

| Tensile Strength at Yield (MPa) | Modulus of Elasticity (MPa) | Polymeric Filler Composition | Peak Peel Strength (N/cm) 10 gsm | Peak Peel Strength (N/cm) 15 gsm | Peak Peel Strength (N/cm) 25 gsm |
|---|---|---|---|---|---|
| 5.76 | 52.1 | Licocene 2502[1] | 0.82 | 1.43 | 1.61 |
| 4.94 | 235 | Licocene 6502[2] | 0.89 | 1.28 | 1.16 |
| 3.53 | 20.6 | L-Modu S410[3] | 0.65 | 1.57 | 2.22 |
| 2.06 | 19.4 | REXtac RT-2830[4] | 0.67 | 1.2 | 1.85 |
| 0.02 | 0.138 | Bostik H2401[5] | 0 | 0 | 0.15 |
| 0.33 | 2.08 | Henkel DM3800[6] | 0.21 | 0.25 | 0.3 |

[1] Available from Clariant
[2] Available from Clariant
[3] Available from Idemitsu
[4] Available from REXtac LLC
[5] Available from Bostik
[6] Available from Henkel Table 3 provides measurements of the Peak Peal Strength for various bond areas comprising various polymeric filler compositions at various gsm amounts after exposure to Desitin® Rapid Relief Cream sold by Johnson & Johnson according to the Laminate Peel Test Method described herein. Table 3 also provides measurements of the Peak Peal Strength for various bond areas comprising various tackified adhesive compositions at various gsm amounts after exposure to Desitin® Rapid Relief Cream sold by Johnson & Johnson according to the Laminate Peel Test Method described herein. The Peak Peel Strength was measured according to the Laminate Peel Test Method described herein.

In addition, Table 3 provides measurements of the Tensile Strength at Yield, according to the Tensile Strength Test Method described herein, and the Modulus of Elasticity, according to the Modulus of Elasticity Test Method described herein for various bond areas comprising various polymeric filler compositions at various gsm amounts. Table 3 also provides measurements of the Tensile Strength at Yield, according to the Tensile Strength Test Method described herein, and the Modulus of Elasticity, according to the Modulus of Elasticity Test Method described herein for various bond areas comprising various tackified adhesive compositions at various gsm amounts.

ADDITIONAL DATA

Bostik Adhesive H2401 and Licocene 2502 Bonding Trial Run Results:
Thickness Measurement
All thickness data was measured using the Mitutoyo Thickness Gage (547-520) and the following protocol:
1) More than 2000 measurement were first taken to determine the thickness of the two un-bonded 15 gsm Top Sheet (FQN Teal GR SPB Embos, IRMS 96731966) and 15 gsm Cuff (Fibertex SMS BLC, IRMS 95743626) web sample layers, and the consistent combined thickness was found to be 240μ.
2) A minimum of 50 data points were then sampled on each TS/Cuff non-woven web sample, looking for the un-bonded areas that are 240μ thick, and then the average of the thickness at the bond sites immediate adjacent to it was taken.

Bonding Conditions
Soft nip pressure—Rubber roll (55 Shore A) against a steel roll, nip between 50-70 psi
HPN nip pressure—Steel roll against a steel roll, nip between 40,000-100,000 psi Tensile Strength: For Base Non-Woven Materials (Cuff, and Top Sheet):

| Items | CD (N/in) | MD (N/in) |
|---|---|---|
| Cuff | 5.2-8.8 | 9.4-16.8 |
| Top Sheet | 7.2-12 | 16.2-21.8 |

Bond Strength: Strong>Good>N (not Acceptable)
Strong—The bonds are stronger than the substrates (100% of the samples pull apart near the bond sites @force >5.2 N/in)
Good—No more than 20% of samples pull apart at the bond sites @force <5.2 N/in, and 80% of the samples pull apart near the bond site @force >5.2 N/in.
(N)—The bonds are weaker than the substrates (100% pull apart at the bond sites @force <5.2 N/in)
Note:
Build up—(BU), Pin Hole—(PH)
Thickness (μ)—Un-Bonded area/Bonded area (BA)

| Test (A) Bonding agent - Bostik Adhesive H2401, coated on 15 gsm Top Sheet and bonded to 15 gsm Cuff | | | | | | | | |
|---|---|---|---|---|---|---|---|---|
| S # | Bar (Soft) | m/s | gsm | BU/PH | ° C. (Sys/Gun) | CD/MD | Thickness (μ) | Matl Penetrat. (μ) |
| 1 | 2.5 (55 psi) | 2 | 20 | N/N | 160/160 | Strong/Good | 240/240 (BA) | 11.69 (TS)  11.66 (Cuff) |
| 2 | 2.5 (55 psi) | 4 | 20 | N/N | 160/160 | Strong/Good | 240/280 (BA) | * (TS)  * (Cuff) |
| S # | Bar (HPN) | m/s | gsm | BU/PH | ° C. (Sys/Gun) | CD/MD | Thickness (μ) | Matl Penetrat. (μ) |
| 1 | 2 (60,000 psi) | 7 | 5 | N/N | 160/160 | N/N | 240/140 (BA) | 3.26 (TS)  3.25 (Cuff) |
| 2 | 2 (60,000 psi) | 7 | 10 | N/N | 160/160 | Good/N | 240/140 (BA) | 6.52 (TS)  6.50 (Cuff) |
| 3 | 2 (60,000 psi) | 7 | 15 | Y/N | 160/160 | Strong/Strong | 240/160 (BA) | 9.45 (TS)  9.42 (Cuff) |
| 4 | 2 (60,000 psi) | 7 | 20 | Y/Y | 160/160 | Strong/Strong | 240/190 (BA) | 12.15 (TS)  12.12 (Cuff) |
| 5 | 2.5 (70,000 psi) | 7 | 20 | Y/N | 160/160 | Strong/Strong | 240/140 (BA) | 13.04 (TS)  12.99 (Cuff) |
| 6 | 2.5 (70,000 psi) | 7 | 5 | N/N | 160/160 | N/N | 240/140 (BA) | 3.26 (TS)  3.25 (Cuff) |
| 7 | 3 (80,000 psi) | 7 | 5 | N/N | 160/160 | N/N | 240/140 (BA) | 3.26 (TS)  3.25 (Cuff) |
| 8 | 3.5 (90,000 psi) | 7 | 5 | N/N | 160/160 | N/N | 240/140 (BA) | 3.26 (TS)  3.25 (Cuff) |
| 9 | 4 (100,000 psi) | 7 | 5 | N/N | 160/160 | N/N | 240/130 (BA) | 3.33 (TS)  3.32 (Cuff) |

| Test (B) Bonding agent - Licocene 2502, coated on 15 gsm TS and bonded to 15 gsm Cuff | | | | | | | | |
|---|---|---|---|---|---|---|---|---|
| S # | Bar (Soft) | m/s | gsm | BU/PH | ° C. (Sys/Gun) | CD/MD | Thickness (μ) | Matl Penetrat. (μ) |
| 1 | 2 (50 psi) | 2 | 10 | N/N | 120/130 | N/N | 240/260 (BA) | * (TS)  * (Cuff) |
| 2 | 2.5 (55 psi) | 7 | 10 | N/N | 120/130 | N/N | 240/260 (BA) | * (TS)  * (Cuff) |
| 3 | 2.5 (55 psi) | 2 | 16 | N/N | 120/130 | N/N | 240/260 (BA) | * (TS)  * (Cuff) |
| 4 | 2 (50 psi) | 2 | 20 | N/N | 120/130 | N/N | 240/290 (BA) | * (TS)  * (Cuff) |
| 5 | 2.5 (55 psi) | 2 | 20 | N/N | 120/130 | Good/Good | 240/260 (BA) | * (TS)  * (Cuff) |
| 6 | 3 (60 psi) | 2 | 20 | N/N | 120/125 | Good/Good | 240/230 (BA) | 13.25 (TS)  13.22 (Cuff) |
| 7 | 3.5 (65 psi) | 2 | 20 | N/N | 120/125 | Good/Good | 240/250 (BA) | 7.44 (TS)  7.42 (Cuff) |
| 8 | 4 (70 psi) | 2 | 20 | N/N | 120/125 | Strong/Strong | 240/270 (BA) | * (TS)  * (Cuff) |

| | Test (B) Bonding agent - Licocene 2502, coated on 15 gsm TS and bonded to 15 gsm Cuff | | | | | | | | |
|---|---|---|---|---|---|---|---|---|---|
| S # | Bar (HPN) | m/s | gsm | BU/PH | °C. (Sys/Gun) | CD/MD | Thickness (μ) | Matl Penetrat. (μ) | |
| 1 | 2 (60,000 psi) | 7 | 5 | N/N | 160/160 | N/N | 240/140 (BA) | 3.67 (TS) | 3.66 (Cuff) |
| 2 | 2.5 (70,000 psi) | 7 | 5 | N/N | 160/160 | N/N | 240/130 (BA) | 3.75 (TS) | 3.74 (Cuff) |
| 3 | 3 (80,000 psi) | 7 | 5 | N/N | 160/160 | N/N | 240/120 (BA) | 3.85 (TS) | 3.83 (Cuff) |
| 4 | 3.5 (90,000 psi) | 7 | 5 | N/N | 160/160 | N/N | 240/110 (BA) | 3.97 (TS) | 3.95 (Cuff) |
| 5 | 4 (100,000 psi) | 7 | 5 | N/N | 160/160 | N/N | 240/100 (BA) | 4.13 (TS) | 4.11 (Cuff) |
| 6 | 1.5 (50,000 psi) | 7 | 8 | Y/N | 140/140 | Good/Good | 240/180 (BA) | 5.53 (TS) | 5.52 (Cuff) |
| 7 | 1.5 (50,000 psi) | 7 | 8 | Y/N | 160/160 | Good/Good | 240/160 (BA) | 5.68 (TS) | 5.66 (Cuff) |
| 8 | 2 (60,000 psi) | 7 | 8 | Y/N | 160/160 | Strong/Strong | 240/180 (BA) | 5.53 (TS) | 5.52 (Cuff) |
| 9 | 1.0 (40,000 psi) | 7 | 10 | Y/N | 120/130 | Good/Good | 240/200 (BA) | 6.78 (TS) | 6.76 (Cuff) |
| 10 | 1.0 (40,000 psi) | 7 | 10 | Y/N | 120/125 | Good/Good | 240/200 (BA) | 6.78 (TS) | 6.76 (Cuff) |
| 11 | 1.5 (50,000 psi) | 7 | 10 | Y/N | 120/130 | Strong/Strong | 240/190 (BA) | 6.84 (TS) | 6.83 (Cuff) |
| 12 | 2 (60,000 psi) | 7 | 10 | Y/N | 160/160 | Strong/Strong | 240/190 (BA) | 6.84 (TS) | 6.83 (Cuff) |
| 13 | 2 (60,000 psi) | 7 | 10 | Y/N | 120/130 | Strong/Strong | 240/190 (BA) | 6.84 (TS) | 6.83 (Cuff) |
| 14 | 2 (60,000 psi) | 7 | 10 | Y/N | 120/125 | Strong/Strong | 240/190 (BA) | 6.84 (TS) | 6.83 (Cuff) |

ADDITIONAL EXAMPLES

A. An absorbent article comprising:
   a) an absorbent core, a first nonwoven material, a second nonwoven material, and a bond area; and
   b) a polymeric filler composition disposed within the bond area;
      wherein the polymeric filler composition comprises less than 1% of a tackifier by weight of the polymeric filler composition;
      wherein the polymeric filler composition is selected from the group consisting of a propylene butene copolymer, a polypropylene homopolymer, a propylene ethylene copolymer, and mixtures thereof;
      wherein the polymeric filler composition has a Tensile Strength at Yield of from about 0.5 MPa to about 10 MPa according to the Tensile Strength Test Method described herein; and
      wherein the bond area has a Peak Peel Strength of from about 0.1 N/cm to about 9 N/cm after exposure to a skin-protecting material for 24 hours according to the Laminate Peel Test Method described herein.

B. The absorbent article of paragraph A, wherein the bond area comprises from 13 gsm to about 30 gsm of the polymeric filler composition; wherein the polymeric filler composition is a polypropylene homopolymer and/or a propylene ethylene copolymer; wherein the skin-protecting material is a first skin-protecting material comprising a mineral oil; wherein the Peak Peel Strength of the bond area is from about 0.15 N/cm to about 1.0 N/cm; and wherein the Tensile Strength at Yield of the polymeric filler composition is from about 4 MPa to about 7 MPa.

C. The absorbent article of paragraph B, wherein the absorbent article has a Modulus of Elasticity of from about 40 MPa to about 500 MPa, according to the Modulus of Elasticity Test Method described herein.

D. The absorbent article of paragraph A, wherein the bond area comprises from about 7 gsm to less than 13 gsm of the polymeric filler composition; wherein the polymeric filler composition is a polypropylene homopolymer and/or a propylene ethylene copolymer; wherein the skin-protecting material is a first skin-protecting material comprising a mineral oil; wherein the Peak Peel Strength of the bond area is from about 0.1 N/cm to about 0.5 N/cm; and wherein the Tensile Strength at Yield of the polymeric filler composition is from about 4 MPa to about 7 MPa.

E. The absorbent article of paragraph D, wherein the absorbent article has a Modulus of Elasticity of from about 40 MPa to about 500 MPa, according to the Modulus of Elasticity Test Method described herein.

F. The absorbent article of paragraph A, wherein the bond area comprises from about 7 gsm to less than 13 gsm of the polymeric filler composition; wherein the polymeric filler composition is a polypropylene homopolymer and/or a propylene butene copolymer; wherein the skin-protecting material is a second skin-protecting material comprising a natural oil and/or a natural extract; wherein the Peak Peel Strength of the bond area is from about 1.15 N/cm to about 2 N/cm; and wherein the Tensile Strength at Yield of the polymeric filler composition is from about 0.5 MPa to about 4.5 MPa.

G. The absorbent article of paragraph F, wherein the absorbent article has a Modulus of Elasticity of from about 5 MPa to about 45 MPa, according to the Modulus of Elasticity Test Method described herein.

H. The absorbent article of paragraph A, wherein the bond area comprises from 13 gsm to about 30 gsm of the polymeric filler composition; wherein the polymeric filler composition is a polypropylene homopolymer and/or a propylene butene copolymer; wherein the skin-protecting material is a second skin-protecting material comprising a natural oil and/or a natural extract; wherein the Peak Peel Strength of the bond area is from about 1.8 N/cm to about 3.0 N/cm; and wherein the Tensile Strength at Yield of the polymeric filler composition is from about 0.5 MPa to about 4.5 MPa.

I. The absorbent article of paragraph H, wherein the absorbent article has a Modulus of Elasticity of from about 5 MPa to about 45 MPa, according to the Modulus of Elasticity Test Method described herein.

J. The absorbent article of paragraph A, wherein the bond area comprises from about 5 gsm to about 30 gsm of the polymeric filler composition; wherein the skin-protecting material is a third skin-protecting material comprising a petroleum based material selected from the group consisting of a petrolatum, a petrolatum jelly, a white petrolatum, a soft petrolatum, a soft paraffin or paraffin wax, a multi-hydrocarbon, and mixtures thereof; wherein the Peak Peel Strength of the bond area is from about 0.4 N/cm to about 3.0 N/cm; and wherein the Tensile Strength at Yield of the polymeric filler composition is from about 0.5 MPa to about 7 MPa.

K. The absorbent article of paragraph J, wherein the absorbent article has a Modulus of Elasticity of from about 5 MPa to about 400 MPa, according to the Modulus of Elasticity Test Method described herein.

L. The absorbent article of paragraph A, wherein the bond area comprises from about 20 gsm to about 30 gsm of the polymeric filler composition; wherein the skin-protecting material is a third skin-protecting material comprising a petroleum based material selected from the group consisting of a petrolatum, a petrolatum jelly, a white petrolatum, a soft petrolatum, a soft paraffin or paraffin wax, a multi-hydrocarbon, and mixtures thereof; wherein the Peak Peel Strength of the bond area is from about 1.75 N/cm to about 3.0 N/cm; and wherein the Tensile Strength at Yield of the polymeric filler composition is from about 1 MPa to about 4 MPa.

M. The absorbent article of paragraph L, wherein the absorbent article has a Modulus of Elasticity of from about 5 MPa to about 45 MPa, according to the Modulus of Elasticity Test Method described herein.

N. The absorbent article of any preceding paragraph, wherein the polymeric filler composition is free of a tackifier.

O. A method comprising:
  a) providing an absorbent article comprising a chassis;
    wherein the chassis comprises an absorbent core, a first nonwoven material, a second nonwoven material, and a bond area;
    wherein the bond area comprises a portion of the first nonwoven material, a portion of the second nonwoven material, and a polymeric filler composition;
    wherein the polymeric filler composition is disposed within the bond area;
    wherein the polymeric filler composition comprises less than 1% of a tackifier by weight of the polymeric filler composition;
    wherein the polymeric filler composition is selected from the group consisting of a propylene butene copolymer, a polypropylene homopolymer, a propylene ethylene copolymer, and mixtures thereof; and
    wherein the polymeric filler composition has a Tensile Strength at Yield of from about 0.5 MPa to about 10 MPa according to the Tensile Strength Test Method described herein;
  b) bringing the bond area in contact with a skin-protecting material;
    wherein the bond area has a Peak Peel Strength of from about 0.1 N/cm to about 9 N/cm after exposure to the skin-protecting material for 24 hours according to the Laminate Peel Test Method described herein.

P. The method of paragraph O, wherein the bond area comprises from 13 gsm to about 30 gsm of the polymeric filler composition; wherein the polymeric filler composition is a polypropylene homopolymer and/or a propylene ethylene copolymer; wherein the skin-protecting material is a first skin-protecting material comprising a mineral oil; wherein the Peak Peel Strength of the bond area is from about 0.15 N/cm to about 1.0 N/cm; and wherein the Tensile Strength at Yield of the polymeric filler composition is from about 4 MPa to about 7 MPa.

Q. The method of paragraph P, wherein the absorbent article has a Modulus of Elasticity of from about 40 MPa to about 500 MPa, according to the Modulus of Elasticity Test Method described herein.

R. The method of paragraph O, wherein the bond area comprises from about 7 gsm to less than 13 gsm of the polymeric filler composition; wherein the polymeric filler composition is a polypropylene homopolymer and/or a propylene ethylene copolymer; wherein the skin-protecting material is a first skin-protecting material comprising a mineral oil; wherein the Peak Peel Strength of the bond area is from about 0.1 N/cm to about 0.5 N/cm; and wherein the Tensile Strength at Yield of the polymeric filler composition is from about 4 MPa to about 7 MPa.

S. The method of paragraph R, wherein the absorbent article has a Modulus of Elasticity of from about 40 MPa to about 500 MPa, according to the Modulus of Elasticity Test Method described herein.

T. The method of paragraph O, wherein the bond area comprises from about 7 gsm to less than 13 gsm of the polymeric filler composition; wherein the polymeric filler composition is a polypropylene homopolymer and/or a propylene butene copolymer; wherein the skin-protecting material is a second skin-protecting material comprising a natural oil and/or a natural extract; wherein the Peak Peel Strength of the bond area is from about 1.15 N/cm to about 2 N/cm; and wherein the Tensile Strength at Yield of the polymeric filler composition is from about 0.5 MPa to about 4.5 MPa.

U. The method of paragraph T, wherein the absorbent article has a Modulus of Elasticity of from about 5 MPa to about 45 MPa, according to the Modulus of Elasticity Test Method described herein.

V. The method of paragraph O, wherein the bond area comprises from 13 gsm to about 30 gsm of the polymeric filler composition; wherein the polymeric filler composition is a polypropylene homopolymer and/or a propylene butene copolymer; wherein the skin-protecting material is a second skin-protecting material comprising a natural oil and/or a natural extract; wherein the Peak Peel Strength of the bond area is from about 1.8 N/cm to about 3.0 N/cm; and wherein the Tensile Strength at Yield of the polymeric filler composition is from about 0.5 MPa to about 4.5 MPa.

W. The method of paragraph V, wherein the absorbent article has a Modulus of Elasticity of from about 5 MPa to about 45 MPa, according to the Modulus of Elasticity Test Method described herein.

X. The method of paragraph O, wherein the bond area comprises from about 5 gsm to about 30 gsm of the polymeric filler composition; wherein the skin-protecting material is a third skin-protecting material comprising a petroleum based material selected from the group consisting of a petrolatum, a petrolatum jelly, a white petrolatum, a soft petrolatum, a soft paraffin or paraffin wax, a multi-hydrocarbon, and mixtures thereof; wherein the Peak Peel Strength of the bond area is from about 0.4 N/cm to about 3.0 N/cm; and wherein the Tensile Strength at Yield of the polymeric filler composition is from about 0.5 MPa to about 7 MPa.

Y. The method of paragraph X, wherein the absorbent article has a Modulus of Elasticity of from about 5 MPa to about 400 MPa, according to the Modulus of Elasticity Test Method described herein.

Z. The method of paragraph O, wherein the bond area comprises from about 20 gsm to about 30 gsm of the polymeric filler composition; wherein the skin-protecting material is a third skin-protecting material comprising a petroleum based material selected from the group consisting of a petrolatum, a petrolatum jelly, a white petrolatum, a soft petrolatum, a soft paraffin or paraffin wax, a multi-hydrocarbon, and mixtures thereof; the Peak Peel Strength of the bond area is from about 1.75 N/cm to about 3.0 N/cm; and wherein the Tensile Strength at Yield of the polymeric filler composition is from about 1 MPa to about 4 MPa.

AA. The method of paragraph Z, wherein the absorbent article has a Modulus of Elasticity of from about 5 MPa to about 45 MPa, according to the Modulus of Elasticity Test Method described herein.

BB. The method of any of paragraphs O-Z, wherein the polymeric filler composition is free of a tackifier.

Test Methods

Laminate Peel Test Method

In the Laminate Peel Test Method, bonded laminates prepared from roll stock are peeled in a tensile tester to determine Peak Peel Strength using a procedure that closely follows ASTM D1876-08. Laminates can be exposed to a skin-protecting materials prior to peel to determine the Peak Peel Strength of a bond area after exposure to the skin-protecting material.

Preparation of Laminate:

A first nonwoven material and a second nonwoven material are affixed via a specified slot coating process using a bonding material to form a laminate. The bonding material may be a polymeric filler composition or a tackified adhesive composition. The first nonwoven material and the second nonwoven material used to form the laminate are 15 gsm polypropylene spunbond (SSS) with a thermal bond pattern matching that of US Design Patent D714,560 that covers approximately 13-15% of first nonwoven material and the second nonwoven material. The first nonwoven material and the second nonwoven material are provided in roll stock form and are 230 mm in width.

The bonding material is slot coated onto the first nonwoven material at a speed of 114 m/min and the total tension at the point of application is 0.5 lbs (10.5 N/m tension per unit width).

The bonding material is slot coated onto the first nonwoven material using an ITW Dynatec APEX Slot Die, from ITW Dynatec, Hendersonville TN, USA, or equivalent). The shim of the die is 0.15 mm thick and cut such that a coating of bonding material is applied in the cross-machine direction of 27 mm width and continuous in the machine direction. The bonding material flow rate for the nozzle is set such that the applied basis weight can be chosen, e.g., 10, 15, or 25±0.1 gsm.

The bonding material is maintained at a temperature ±5° C. at all points up to and including the applicator such that the viscosity of the of bonding material at the maintained temperature is within the range of 1,500 mPa·s to 10,000 mPa·s.

The overall slot coating process is performed at an ambient temperature of 21±2° C. The bonding material is applied to the first nonwoven material with the slot coat die by bringing the slot coat die into contact with the first nonwoven material supported between two non-driven web-support idlers that co-rotate with the moving first nonwoven material. Each web-support idler has a 50 mm diameter. The spacing of the web-support idlers is set to 200 mm, center to center, and the bonding material applicator's exit is set at a point 150 mm from the downstream idler's center. The bonding material applicator is pressed into the tensioned first nonwoven material between the idlers, such that the first nonwoven material is deflected 3-4 mm at the exit point of the bonding material from the slot coat die, with respect to the plane made by the first nonwoven material under tension when the bonding material applicator is absent. The angle made between the slot coat die's shim plane and the plane of the tensioned first nonwoven material when the bonding material applicator is not engaged is the pitch angle. This angle is described to be zero pitch when the planes are perpendicular to each other. During application of the bonding material to the first nonwoven material, the angle is set to zero pitch. In other words, the plane of the shim relative to the plane of the tensioned first nonwoven material when the bonding material applicator is not engaged is 900 on the side of the downstream web-support idler. The bonding material coating is centered along the length of the first nonwoven material by centering the width of the slot coat die on the cross-machine width of the first nonwoven material.

The coated first nonwoven material is then brought into contact with the second nonwoven material 165 mm after the point of coating with the bonding material to create a laminate. A compression nip is used to compress the laminate at a point 955 mm from the point of coating with the bonding material. The compression nip consists of a steel roll and a rubber coated steel roll that coaxially counter rotate while in contact with each other to create pressure between them. The steel roll and rubber roll diameters are 100 mm and the rubber coating is 20 mm thick with a Shore A hardness of 100. The steel roll and rubber coated steel roll are forced together to develop a constant pressure of 70 psi in the nip. The laminate travels through the nip and is subjected to this pressure as it travels. The laminate speed and the resulting bonded laminate is maintained at 114 m/min. After passing through the compression nip, the bonded laminate is wound onto a roll for sampling at 1.5 lbs winding tension. Laminated test panels are immediately cut from the wound roll of bonded laminate. The laminated test panels are equilibrated at 21±2° C. and 40% relative humidity for a minimum of 24 hours before further preparation and testing.

25 mm-wide bonded laminate test specimens are cut from the laminated test panels as described in ASTM D1876-08. If the bonded laminate specimens are not to be exposed to a skin-protecting material prior to peel measurement, analysis proceeds via the steps described in the Preconditioning and Measurement section of this method. If the bonded laminate is to be exposed to a skin-protecting material prior to peel measurement, the following additional sample preparation steps are followed to facilitate skin-protecting material exposure.

A skin-protecting material and the bonded laminate test specimen(s) are pre-conditioned for at least 24 hours at a relative humidity of 50±2% and at 23±1° C. After pre-conditioning, the skin-protecting material is applied to the bond area of the bonded laminate test specimen in an excess amount. Excess is defined as the greater of (1) three times the combined basis weight of the substrates and the bonding material or (2) 400 grams per square meter (gsm). The skin-protecting material is spread evenly onto both sides of the bonded laminate test specimen in the region that corresponds to the bond area. The application of the skin-protecting material is carried out under a relative humidity of 50±2% and at 23±1° C.

Preconditioning and Measurement:

Each bonded laminate test specimen, with or without skin-protecting material treatment, is placed into a glass jar, sealed, and aged for 24 hours at 37±1° C. in a convection oven. After aging, the sealed glass jar(s) containing the bonded laminate test specimen(s) are removed from the oven and opened. Each bonded laminate test specimen is conditioned for 24 hours at a relative humidity of 50±2% and at 23±1° C. before testing Peak Peel Strength.

The Peak Peel Strength of a bond area within the bonded laminate test specimen is determined by continuing to follow the T-Peel Test Method, ASTM D1876-08, with the following additional guidance. A suitable device for determining the peel strength is a universal testing system, such as a MTS Alliance series from MTS Systems Corporation, Eden Prairie, MN, or equivalent. The constant head speed is 305 mm/min, the initial grip separation is 50 mm, peel force is recorded for the crosshead travel distance corresponding to the extent in the peel direction of the bond area of the bonded laminate, and the Peak Peel Strength of a bond area is the maximum recorded peeling load value determined in newtons per centimeter of specimen width (N/cm), and each reported Peak Peel Strength of a bond area is an arithmetic mean of five to ten tests.

Tensile Strength at Yield Test Method

The Tensile Strength of a bonding material, a tackified adhesive composition, or a polymeric filler composition is determined using the Standard Test Method for Tensile Properties of Plastics, which consists of performing ASTM D638-14 with the following additional guidance. Ambient conditions are maintained at relative humidity of 50±2% and at 23±1° C. Polymers and hot melt adhesive compositions are cast into a shape consistent with a Type IV "dogbone" as described in FIG. 1 of ASTM D638-14 and allowed to cool to ambient conditions before conditioning the test specimens in accordance with Procedure A of ASTM Practice D618. The test proceeds with a crosshead speed of 50 mm/min.

Tensile Strength at Yield is calculated as described in section 11.2 of ASTM D638-14 and is reported as the "Tensile Strength at Yield" in units of megapascals (MPa) to the nearest 0.01 MPa.

Modulus of Elasticity Test Method

The Modulus of Elasticity of a bonding material, a tackified adhesive composition, or a polymeric filler composition is determined using the Standard Test Method for Tensile Properties of Plastics, which consists of performing ASTM D638-14 with the following additional guidance. Ambient conditions are maintained at relative humidity of 50±2% and at 23±1° C. Polymers and hot melt adhesive compositions are cast into a shape consistent with a Type IV "dogbone" as described in FIG. 1 of ASTM D638-14 and allowed to cool to ambient conditions before conditioning the test specimens in accordance with Procedure A of ASTM Practice D618. The test proceeds with a crosshead speed of 50 mm/min.

The Modulus of Elasticity is also calculated as described in section 11.4 of ASTM D638-14 and is reported as the "Modulus of Elasticity" in units of MPa to the nearest 0.01 MPa.

Viscosity Test Method

The Viscosity Parameter of a hot melt adhesive composition is determined using the Viscosity Parameter Test Method, which consists of performing ASTM D3236-15 with the following additional guidance. A Brookfield RVT viscometer with spindle SC 4-27 (Brookfield Engineering, Middleboro, MA, USA), or equivalent, is used. The sample temperature is maintained at 170.0±1.0° C., unless otherwise specified, throughout the measurement. The sample is preheated for 10 minutes and stirred with the measurement spindle for 30 min. The spindle is rotated at 20 rpm throughout the measurement. The resulting apparent viscosity, as described in section 10, is reported as the "viscosity" in units of millipascal-seconds to the nearest 100 mPa·s.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a) an absorbent core, a first nonwoven material, a second nonwoven material, and a bond area joining a portion of the first nonwoven material and a portion of the second nonwoven material; and
   b) a polymeric filler composition disposed within the bond area;
      wherein the polymeric filler composition comprises less than 5% of a tackifier by weight of the polymeric filler composition;
      wherein the polymeric filler composition is selected from the group consisting of a propylene butene copolymer, a polypropylene homopolymer, a propylene ethylene copolymer, and mixtures thereof;
      wherein the polymeric filler composition has a Tensile Strength at Yield of from about 0.5 MPa to about 10 MPa according to the Tensile Strength Test Method described herein.

2. The absorbent article of claim 1, wherein the polymeric filler composition is a polypropylene homopolymer and/or a propylene ethylene copolymer.

3. The absorbent article of claim 1, wherein the polypropylene homopolymer has a viscosity of from about 500 mPa·s to about 3,000 mPa·s at 170° C.

4. The absorbent article of claim 1, wherein the propylene ethylene copolymer has a viscosity of from about 1,000 mPa·s to about 5,000 mPa·s at 170° C.

5. The absorbent article of claim 1, wherein the first nonwoven forms a portion of a belt.

6. An absorbent article comprising:
a) an absorbent core, a first nonwoven material, a second nonwoven material, and a bond area joining a portion of the first nonwoven material and a portion of the second nonwoven material; and
b) a polymeric filler composition disposed within the bond area;
   wherein the polymeric filler composition comprises at least 98% of a polymer selected from the group consisting of a propylene butene copolymer, a polypropylene homopolymer, a propylene ethylene copolymer, and mixtures thereof;
   wherein the polymeric filler composition comprises less than 5% of a tackifier by weight of the polymeric filler composition;
   wherein the polymeric filler composition has a Tensile Strength at Yield of from about 0.5 MPa to about 10 MPa according to the Tensile Strength Test Method described herein.

7. The absorbent article of claim 6, wherein the polymeric filler composition is a polypropylene homopolymer and/or a propylene ethylene copolymer.

8. The absorbent article of claim 6, wherein the polymeric filler composition further comprises an antioxidant.

9. The absorbent article of claim 6, wherein the polymeric filler composition further comprises a brightener.

10. The absorbent article of claim 6, wherein the polypropylene homopolymer has a viscosity of from about 500 mPa·s to about 3,000 mPa·s at 170° C.

11. The absorbent article of claim 6, wherein the propylene ethylene copolymer has a viscosity of from about 1,000 mPa·s to about 5,000 mPa·s at 170° C.

12. The absorbent article of claim 6, wherein the polymeric filler composition has a Modulus of Elasticity of from about 40 MPa to about 500 MPa.

* * * * *